United States Patent
Lemmon et al.

(10) Patent No.: US 11,981,660 B2
(45) Date of Patent: May 14, 2024

(54) NEURITE OUTGROWTH PROMOTERS AND USES THEREOF

(71) Applicants: UNIVERSITY OF MIAMI, Miami, FL (US); Torrey Pines Institute for Molecular Studies, Port St. Lucie, FL (US)

(72) Inventors: Vance Lemmon, Miami, FL (US); Hassan Al-Ali, Miami, FL (US); John Bixby, Miami, FL (US); Marc Giulianotti, Vero Beach, FL (US)

(73) Assignees: UNIVERSITY OF MIAMI, Miami, FL (US); Torrey Pines Institute for Molecular Studies, Port St. Lucie, FL (US)

( * ) Notice: Subject to any disclaimer, the term of this patent is extended or adjusted under 35 U.S.C. 154(b) by 0 days.

(21) Appl. No.: 16/982,946

(22) PCT Filed: Mar. 21, 2019

(86) PCT No.: PCT/US2019/023391
§ 371 (c)(1),
(2) Date: Sep. 21, 2020

(87) PCT Pub. No.: WO2019/183369
PCT Pub. Date: Sep. 26, 2019

(65) Prior Publication Data
US 2021/0017162 A1 Jan. 21, 2021

Related U.S. Application Data

(60) Provisional application No. 62/646,133, filed on Mar. 21, 2018.

(51) Int. Cl.
*C07D 403/06* (2006.01)
(52) U.S. Cl.
CPC ................... *C07D 403/06* (2013.01)
(58) Field of Classification Search
CPC .................... C07D 403/06; A61K 31/4178
USPC ........................ 548/312.7; 514/392
See application file for complete search history.

(56) References Cited

U.S. PATENT DOCUMENTS 5,750,553 A   5/1998   Claussner et al.
2009/0176766 A1   7/2009   Chern et al.

OTHER PUBLICATIONS

Acharya, et al., Journal of Combinatorial Chemistry (2001), 3(6), 612-623. (Year: 2001).*
Al-Ali et al., In vitro models of axon regeneration, Exp. Neurol., 287:423-434 (2017).
Berge et al., Pharmaceutical salts, J. Pharm. Sci., 66(1):1-19 (1977).
Chang et al., Glaucoma 2.0: neuroprotection, neuroregeneration, neuroenhancement, Ophthalmology, 119(5):979-986 (2012).
Dekosky et al., Traumatic brain injury-football, warfare, and long-term effects, N. Engl. J. Med., 363(14):1293-1296 (2010).
Fitzgerald et al., Repair in the central nervous system, J. Bone Joint Surg. Br., 89(11):1413-1420 (2007).
Haines et al., Axonal Damage in Multiple Sclerosis, Mt. Sinai J. Med. A J. Transl. Pers. Med., 78 (2), 231-243 (2011).
International Application No. PCT/US19/23391, International Preliminary Report on Patentability, dated Oct. 1, 2020.
International Application No. PCT/US19/23391, International Search Report and Written Opinion, dated Jul. 18, 2019.
Meberg et al., Culturing hippocampal and cortical neurons, Methods cell Biol., 71:111-127 (2003).
Medana et al., Axonal damage: a key predictor of outcome in human CNS diseases, Brain, 126(3):515-530 (2003).
Nefzi et al., Synthesis of dihydroimidazole tethered imidazolinethiones and their activity as novel antagonists of the nuclear retinoic acid receptor-related orphan receptors (RORs), Bio. Med. Chem. Lett., 27:1608-1610 (2017).
Silva et al., From basics to clinical: a comprehensive review on spinal cord injury, Prog. Neurobiol., 114:25-57 (2014).
Vrabec et al., The neurobiology of cell death in glaucoma, Eye, 21:S11-S14 (2007).
Young, Spinal cord regeneration, Cell Transplant., 23(4):573-611 (2014).

* cited by examiner

*Primary Examiner* — Jeffrey H Murray
(74) *Attorney, Agent, or Firm* — MARSHALL, GERSTEIN & BORUN LLP

(57) ABSTRACT

Provided herein are compounds useful in treating a central nervous system disorder associated with neuronal and/or axonal damage, methods for their preparation, and related pharmaceutical compositions. For example provided herein are compounds of Formula (I): and pharmaceutically acceptable salts and compositions including the same.

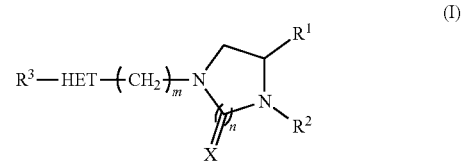

(I)

19 Claims, No Drawings

NEURITE OUTGROWTH PROMOTERS AND USES THEREOF

BACKGROUND

Field of the Disclosure

Provided herein are compounds useful in treating a central nervous system disorder associated with neuronal and/or axonal damage.

Description of Related Technology

Recovery from spinal cord injury ("SCI") is limited by the inability of central nervous system ("CNS") neurons to regenerate their damaged axons. Traumatic brain injury, for example, can produce lifelong psychological and cognitive deficits (see DeKosky et al., N. Engl. J. Med. 2010, 363 (14), 1293-1296), while spinal cord injuries can result in permanent paralysis. See Silva et al., Prog. Neurobiol. 2014, 114, 25-57. In addition to mechanical injury, CNS axons can be damaged by degenerative neuropathies including glaucoma (see Vrabec et al., Eye 2007, 21, S11-514), multiple sclerosis (see Haines et al., Mt. Sinai J. Med. A J. Transl. Pers. Med. 2011, 78 (2), 231-243), Alzheimer's disease, and Parkinson's disease. As such, promoting regeneration of CNS axons is an attractive therapeutic strategy with clinical applicability in a wide range of indications. See Medana et al., Brain 2003, 126 (3), 515-530; Fitzgerald et al., J. Bone Joint Surg. Br. 2007, 89 (11), 1413-1420; Young, Cell Transplant. 2014, 23 (4), 573-611; and Chang et al., Ophthalmology 2012, 119 (5), 979-986. Because the etiology of axon regeneration failure is complex and multifactorial, the development of new neurite outgrowth promoters to treat injuries and diseases associated with SCI and degenerative neuropathies has traditionally been challenging. See Young et al., Cell Transplant. 2014, 23 (4), 573-611; Al-Ali, H. et al., Exp. Neurol. 2017, 287, 423-434.

Thus, a need exists for new compounds that can stimulate axon regeneration.

SUMMARY

Provided herein are compounds of Formula (I), or pharmaceutically acceptable salts thereof:

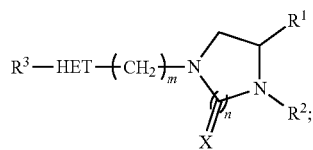

(I)

wherein: m is 3, 4, or 5; n is 1 or 2; HET is $C_{3-7}$heterocycloalkyl; each X independently is S or O; $R^1$ is $C_{1-6}$alkyl, $C_{0-3}$alkylene-$C_{3-7}$cycloalkyl, $C_{0-3}$alkylene-$C_{3-7}$heterocycloalkyl, $C_{0-3}$alkylene-$C_{6-10}$aryl, or $C_{0-3}$alkylene-$C_{2-6}$heteroaryl; $R^2$ is $C_{1-6}$alkyl, $C_{1-3}$alkylene-$C_{3-7}$cycloalkyl, $C_{1-3}$alkylene-$C_{3-7}$heterocycloalkyl, $C_{1-3}$alkylene-$C_{6-10}$aryl, or $C_{1-3}$alkylene-$C_{2-6}$heteroaryl; and $R^3$ is $C_{1-8}$alkyl, $C_{0-3}$alkylene-$C_{3-7}$cycloalkyl, $C_{0-3}$alkylene-$C_{3-7}$heterocycloalkyl, $C_{0-3}$alkylene-$C_{6-10}$aryl, or $C_{0-3}$alkylene-$C_{2-6}$heteroaryl; and each heterocycloalkyl, and heteroaryl group independently has 1, 2, or 3 ring heteroatoms selected from N, O, and S.

In some embodiments, m is 3. In various embodiments, m is 4. In some cases, m is 5. In some embodiments, n is 1. In some cases, X is S. In various cases, X is O. In various embodiments, n is 2. In some embodiments, each X is S. In some cases, each X is O. In various cases, one X is S and the other X is O.

In some embodiments, HET comprises dihydroimidazolyl, piperazinyl, diketopiperazinyl, $C_{2-5}$cyclic guanidinyl, $C_{2-5}$cyclic ureayl, $C_{2-5}$cyclic thioureayl, aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, tetrahydropyranyl, tetrahydrothiopyranyl, pyranyl, thiopyranyl, or morpholinyl. In various embodiments, HET comprises dihydroimidazolyl, piperazinyl, diketopiperazinyl, $C_{2-5}$cyclic guanidinyl, $C_{2-5}$cyclic ureayl, or $C_{2-5}$cyclic thioureayl. In some cases, HET is

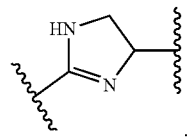 [SMILES: *C1=NC(*)CN1]

In various cases, $R^1$ is $C_{1-6}$alkyl. In some embodiments, $R^1$ is methyl, ethyl, propyl, isopropyl, butyl, 2-butyl, or isobutyl. In various embodiments, $R^1$ is methyl or isobutyl. In some cases, $R^1$ is $C_{0-3}$alkylene-$C_{3-7}$cycloalkyl. In various cases, the cycloalkyl comprises cyclobutyl, cyclopentyl, cyclohexyl, or cycloheptyl, such as $CH_2$-cyclohexyl. In some embodiments, $R^1$ is $C_{0-3}$alkylene-$C_{3-7}$heterocycloalkyl. In various embodiments, the $C_{3-7}$heterocycloalkyl comprises aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, piperazinyl, tetrahydropyranyl, tetrahydrothiopyranyl, pyranyl, thiopyranyl, or morpholinyl. In some cases, $R^1$ is $C_{0-3}$alkylene-$C_{6-10}$aryl. In various cases, $C_{6-10}$aryl comprises phenyl. In some cases, $R^1$ is phenyl, benzyl, 4-fluorophenyl-methyl, or 4-ethoxybenzyl. In some embodiments, $R^1$ is $C_{0-3}$alkylene-$C_{2-6}$heteroaryl. In various embodiments, the $C_{2-6}$heteroaryl comprises pyrrolyl, pyrazolyl, imidazolyl, tetrazolyl, furanyl, thiophenyl, thiazolyl, oxazolyl, isooxazolyl, thiadiazolyl, oxadiazolyl, pyridinyl, pyrazinyl, pyrimidinyl, oxazolyl, or isoxazolyl. In some cases, $R^1$ is 3-methylpyridinyl.

In some embodiments, $R^2$ is $C_{1-6}$alkyl. In various embodiments, $R^2$ is methyl, ethyl, propyl, isopropyl, butyl, s-butyl, isobutyl, t-butyl, pentyl, hexyl, heptyl, or 4-methylpentyl. In some cases, $R^2$ is 4-methylpentyl. In various embodiments, $R^2$ is $C_{1-3}$alkylene-$C_{3-7}$cycloalkyl. In some embodiments, the $C_{3-7}$cycloalkyl comprises cyclobutyl, cyclopentyl, cyclohexyl, or cycloheptyl. In some embodiments, $R^2$ is selected from the group consisting of

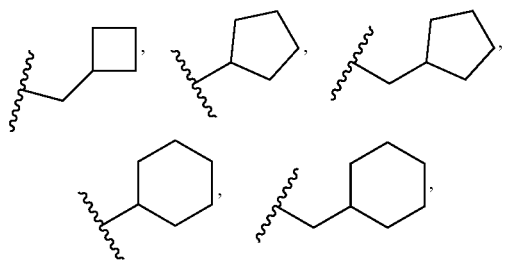

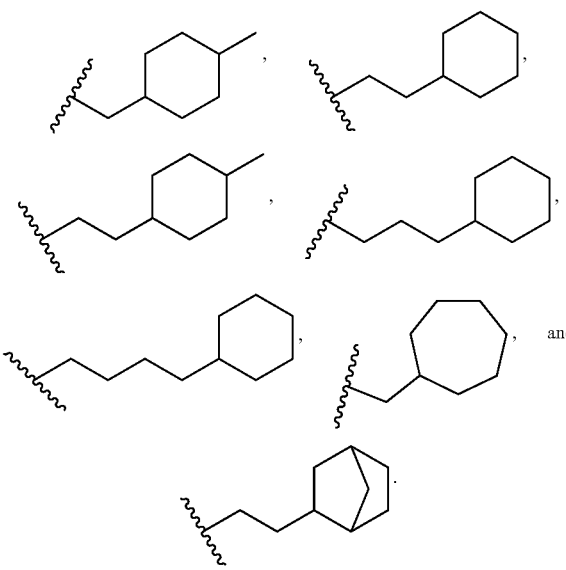

In various embodiments, R² is selected from the group consisting of

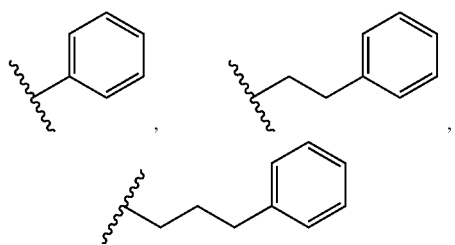

In some cases, R² is $C_{1-3}$alkylene-$C_{3-7}$heterocycloalkyl. In various cases, the $C_{3-7}$heterocycloalkyl comprises aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, piperazinyl, tetrahydropyranyl, tetrahydrothiopyranyl, pyranyl, thiopyranyl, or morpholinyl. In some embodiments, R² is $C_{1-3}$alkylene-$C_{6-10}$aryl or $C_{1-3}$alkylene-$C_{2-6}$heteroaryl. In various embodiments, the $C_{6-10}$aryl group comprises phenyl and the $C_{2-6}$heteroaryl comprises pyrrolyl, pyrazolyl, imidazolyl, tetrazolyl, furanyl, thiophenyl, thiazolyl, oxazolyl, isooxazolyl, thiadiazolyl, oxadiazolyl, pyridinyl, pyrazinyl, pyrimidinyl, oxazolyl, or isoxazolyl. In some cases, R² is

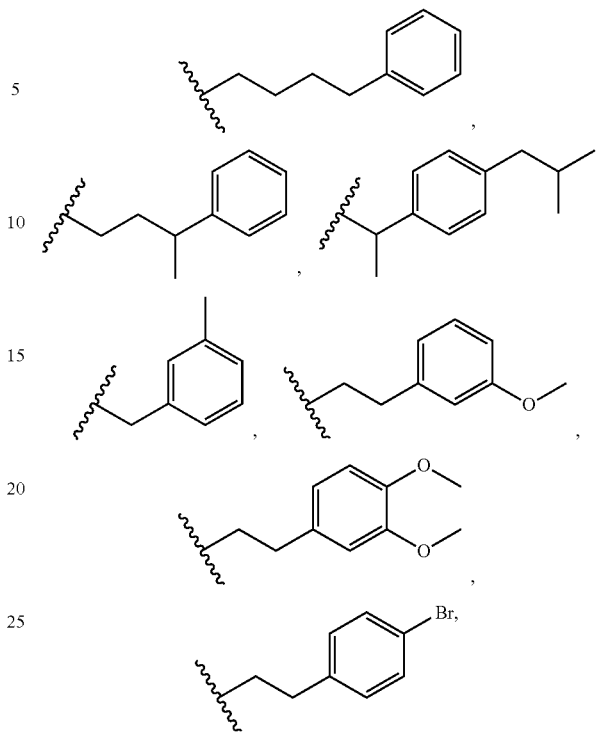

In various cases, R³ is $C_{1-8}$alkyl. In some embodiments, R³ is methyl, ethyl, propyl, isopropyl, butyl, s-butyl, isobutyl, t-butyl, 2-methylbutyl, 3-methylbutyl, 4-methylpentyl. In various embodiments, R³ is s-butyl. In some cases, R³ is $C_{0-3}$alkylene-$C_{3-7}$cycloalkyl. In various cases, the $C_{3-7}$cycloalkyl comprises cyclopentyl or cyclohexyl. In some embodiments, R³ is

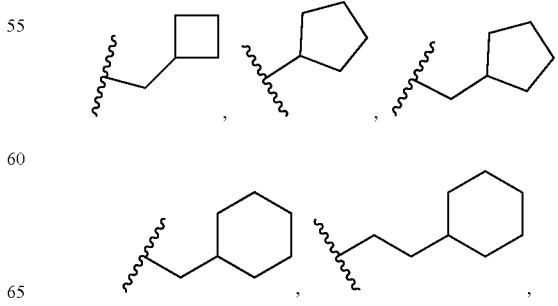

-continued

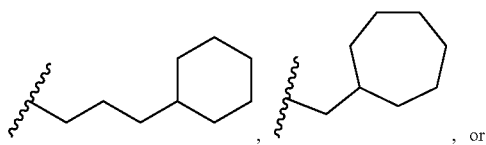

, or

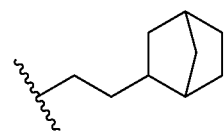

In various cases, R³ is

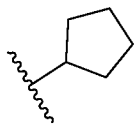

In some embodiments, R³ is C₀₋₃alkylene-C₃₋₇heterocycloalkyl. In some embodiments, C₃₋₇heterocycloalkyl comprises aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, piperazinyl, tetrahydropyranyl, tetrahydrothiopyranyl, pyranyl, thiopyranyl, or morpholinyl. In various embodiments, R³ is C₁₋₃alkylene-C₆₋₁₀aryl or C₁₋₃alkylene-C₂₋₆heteroaryl. In some cases, the C₆₋₁₀aryl group comprises phenyl and the C₂₋₆heteroaryl comprises pyrrolyl, pyrazolyl, imidazolyl, tetrazolyl, furanyl, thiophenyl, thiazolyl, oxazolyl, isooxazolyl, thiadiazolyl, oxadiazolyl, pyridinyl, pyrazinyl, pyrimidinyl, oxazolyl, or isoxazolyl. In some embodiments, R³ is

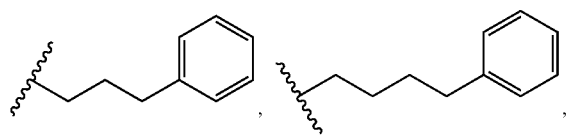

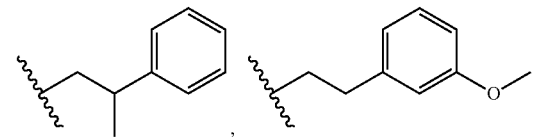

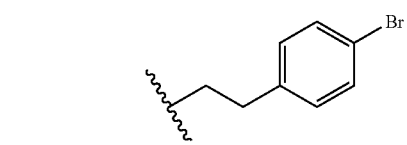

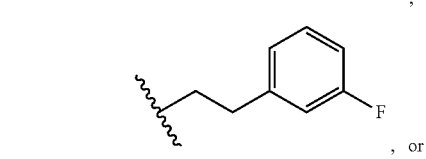

, or

-continued

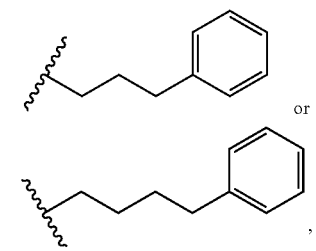

In various cases, R³ is

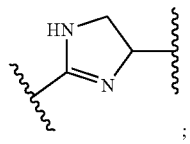 [SMILES: *C1=NC(*)CN1]

or

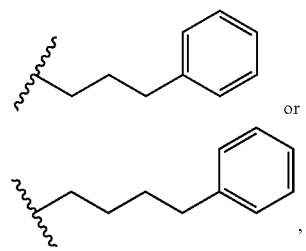

,

In some embodiments, m is 4; n is 1; X is S; HET is

R¹ is C₁₋₆alkyl or C₀₋₃alkylene-C₆₋₁₀aryl; R² is C₁₋₃alkylene-C₃₋₇cycloalkyl, and R³ is C₁₋₆alkyl, C₀₋₃alkylene-C₃₋₇cycloalkyl, or C₁₋₃alkylene-C₆₋₁₀aryl. Some specifically contemplated compounds of the disclosure are listed in Table A. In some cases, the compounds of the disclosure are selected from the group consisting of

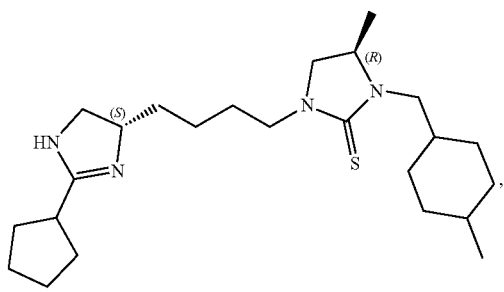

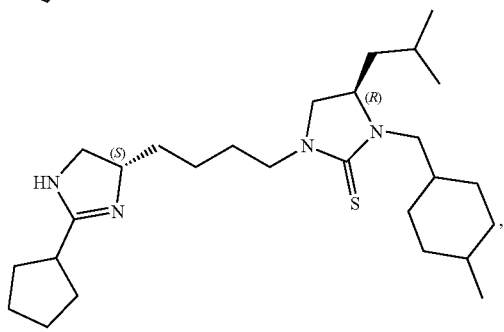

,

-continued

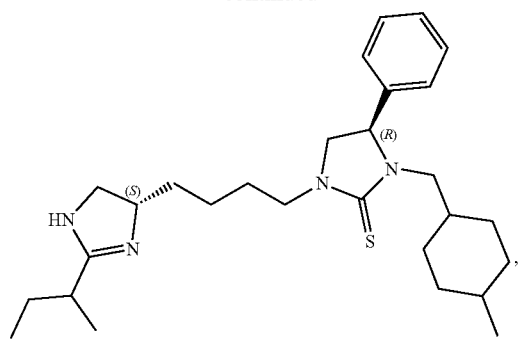

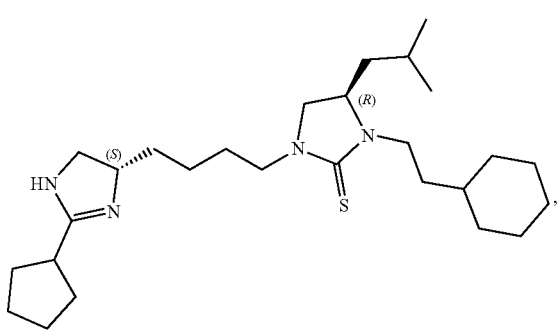

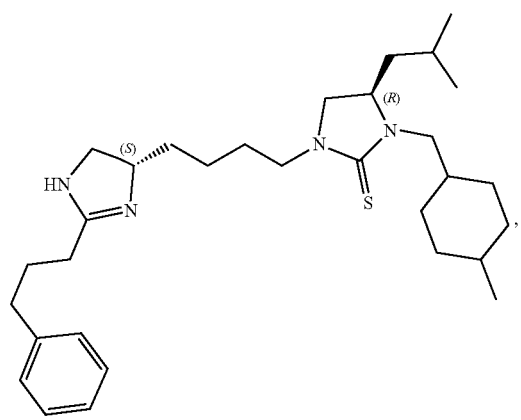

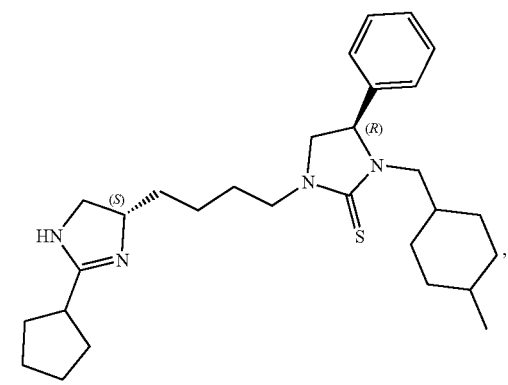

-continued

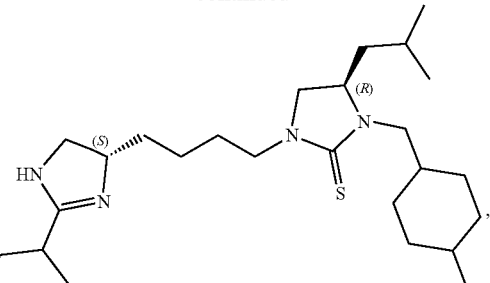

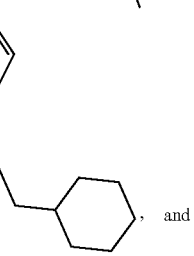

, and

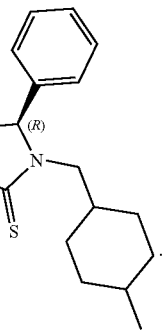

.

Further provided herein are pharmaceutical compositions comprising the compounds of the disclosure, or salts thereof, and a pharmaceutically acceptable excipient.

Also provided are methods of inducing neurite growth by contacting neurites with a compound as disclosed herein or salt thereof. Further provided are methods of treating a CNS disorder associated with neuronal and/or axonal damage in a subject by administering a compound as disclosed herein or salt thereof in an amount effective to repair neuronal and/or axonal damage and thereby treat the CNS disorder. In some cases, the CNS disorder is paralysis, spinal cord injury, optic nerve injury, glaucoma, multiple sclerosis, traumatic brain injury, diffuse axonal injury, stroke, or a degenerative disease (such as Parkinson's disease).

Further provided are methods of treating a peripheral nervous system (PNS) disorder associated with neuronal and/or axonal damage in a subject by administering a compound as disclosed herein or salt thereof in an amount effective to repair neuronal and/or axonal damage and thereby treat the PNS disorder. In some cases, the PNS disorder is peripheral nerve trauma, repetitive stress, amyotrophic lateral sclerosis (ALS), erectile dysfunction, a disorder associated with an organ transplant, neurofibromatosis, blood vessel disease, diabetes, an autoimmune disorder, a disorder associated with chemical toxicity, or kidney disease.

Also provided are methods of treating nerve degeneration in a subject undergoing cancer therapy, comprising administering a compound as disclosed herein or a salt thereof in an amount effective to treat the nerve degeneration.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Provided herein are compounds, or pharmaceutically acceptable salts thereof, having a structure of Formula (I):

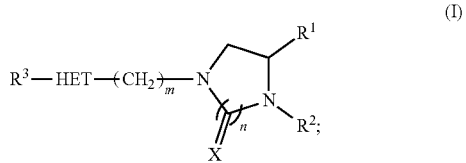

(I)

wherein: m is 3, 4, or 5; n is 1 or 2; HET is $C_{3-7}$heterocloalkyl; each X independently is S or O; $R^1$ is $C_{1-6}$alkyl, $C_{0-3}$alkylene-$C_{3-7}$cycloalkyl, $C_{0-3}$alkylene-$C_{3-7}$heterocyloalkyl, $C_{0-3}$alkylene-$C_{6-10}$aryl, or $C_{0-3}$alkylene-$C_{2-6}$heteroaryl; $R^2$ is $C_{1-6}$alkyl, $C_{1-3}$alkylene-$C_{3-7}$cycloalkyl, $C_{1-3}$alkylene-$C_{3-7}$heterocycloalkyl, $C_{1-3}$alkylene-$C_{6-10}$aryl, or $C_{1-3}$alkylene-$C_{2-6}$heteroaryl; and $R^3$ is $C_{1-8}$alkyl, $C_{0-3}$alkylene-$C_{3-7}$cycloalkyl, $C_{0-3}$alkylene-$C_{3-7}$heterocycloalkyl, $C_{0-3}$alkylene-$C_{6-10}$aryl, or $C_{0-3}$alkylene-$C_{2-6}$heteroaryl; and each heterocycloalkyl and heteroaryl group independently has 1, 2, or 3 ring heteroatoms selected from N, O, and S.

The compounds disclosed herein can promote neurite outgrowth by several fold relative to control, and exhibit remarkable potency. For example, the compounds disclosed herein can induce neurite outgrowth by 200% relative to a control compound, and can exhibit nanomolar potency.

Chemical Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to a bivalent saturated aliphatic radical. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "heterocycloalkyl" is defined similarly as cycloalkyl, except the ring contains one to three heteroatoms independently selected from oxygen, nitrogen, and sulfur. For example, $C_3$-$C_7$heterocycloalkyl refers to a cyclic ring having three to seven ring carbon atoms and one to three ring heteroatoms selected from nitrogen, oxygen, and sulfur (i.e., a four to ten membered ring). Nonlimiting examples of heterocycloalkyl groups include piperdine, tetrahydrofuran, tetrahydropyran, dihydrofuran, morpholine, oxazepaneyl, and the like. Cycloalkyl and heterocycloalkyl groups can be saturated or partially unsaturated ring systems optionally substituted with, for example, one to three groups, independently selected alkyl, alkyleneOH, C(O)NH₂, NH₂, oxo (=O), aryl, haloalkyl, halo, and OH. Heterocycloalkyl groups optionally can be further N-substituted as described herein.

As used herein, the term "$C_{2-5}$cyclic guanidinyl" refers to a heterocyclyl group comprising a guanidinyl moiety having 2, 3, 4, or 5 ring carbon atoms

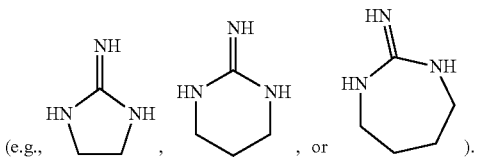 [SMILES: N=C1NCCN1 ; N=C1NCCCN1 ; N=C1NCCCCN1]

Unless otherwise indicated, the $C_{2-5}$cyclic guanidinyl group can be unsubstituted or substituted.

As used herein, the term "$C_{2-5}$cyclic ureayl" refers to a heterocyclyl group comprising a ureayl moiety having 2, 3, 4, or 5 ring carbon atoms

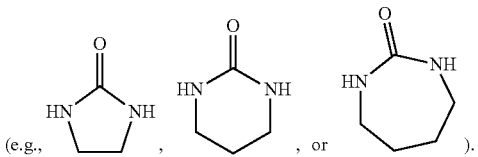

Unless otherwise indicated, the $C_{2-5}$cyclic ureayl group can be unsubstituted or substituted.

As used herein, the term "$C_{2-5}$cyclic thioureayl" refers to a heterocyclyl group comprising a thioureayl moiety having 2, 3, 4, or 5 ring carbon atoms (e.g., 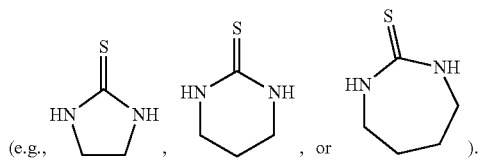 [SMILES: O=C1NCCN1 ; O=C1NCCCN1 ; O=C1NCCCCN1]).

Unless otherwise indicated, the $C_{2-5}$cyclic thioureayl group can be unsubstituted or substituted.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to three ring atoms are selected from oxygen, nitrogen, and sulfur, and the remaining ring atoms are carbon, said ring system being joined to the remainder of the molecule by any of the ring atoms. For example, a $C_{2-6}$heteroaryl refers to a monocyclic or polycyclic aromatic ring system having two to six ring carbon atoms and one to three heteroatoms, and is a five to nine membered ring system. Nonlimiting examples of heteroaryl groups include, but are not limited to, pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thienyl, quinolinyl, isoquinolinyl, benzoxazolyl, benzimidazolyl, benzofuranyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group.

A "substituted" functional group (e.g., a substituted alkyl, alkyleneyl, cycloalkyl, aryl, or heteroaryl) is a functional group having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, sulfhydryl, and halo. When a substituted alkyl group includes more than one non-hydrogen radical, the substituents can be bound to the same carbon or two or more different carbon atoms.

Compounds of Formula (I)

Disclosed herein are compounds, or pharmaceutically acceptable salts thereof, having a structure of Formula (I):

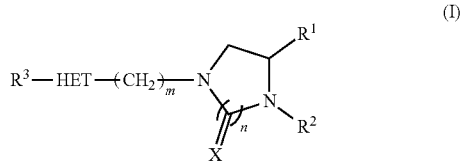

(I)

wherein: m is 3, 4, or 5; n is 1 or 2; HET is $C_{3-7}$heterocycloalkyl; each X independently is S or O; $R^1$ is $C_{1-6}$alkyl, $C_{0-3}$alkylene-$C_{3-7}$cycloalkyl, $C_{0-3}$alkylene-$C_{3-7}$heterocycloalkyl, $C_{0-3}$alkylene-$C_{6-10}$aryl, or $C_{0-3}$alkylene-$C_{2-6}$heteroaryl; $R^2$ is $C_{1-6}$alkyl, $C_{1-3}$alkylene-$C_{3-7}$cycloalkyl, $C_{1-3}$alkylene-$C_{3-7}$heterocycloalkyl, $C_{1-3}$alkylene-$C_{6-10}$aryl, or $C_{1-3}$alkylene-$C_{2-6}$heteroaryl; and $R^3$ is $C_{1-8}$alkyl, $C_{0-3}$alkylene-$C_{3-7}$cycloalkyl, $C_{0-3}$alkylene-$C_{3-7}$heterocycloalkyl, $C_{0-3}$alkylene-$C_{6-10}$aryl, or $C_{0-3}$alkylene-$C_{2-6}$heteroaryl; and each heterocycloalkyl, and heteroaryl group independently has 1, 2, or 3 ring heteroatoms selected from N, O, and S.

In some embodiments, m is 3. In various embodiments, m is 4. In some cases, m is 5.

In some embodiments, n is 1. In some cases, X is S. In various cases, X is O.

In various embodiments, n is 2. In some embodiments, each X is S. In some cases, each X is O. In various cases, one X is S and the other X is O.

In some embodiments, HET comprises dihydroimidazolyl, piperazinyl, diketopiperazinyl, $C_{2-5}$cyclic guanidinyl, $C_{2-5}$cyclic ureayl, $C_{2-5}$cyclic thioureayl, aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, tetrahydropyranyl, tetrahydrothiopyranyl, pyranyl, thiopyranyl, or morpholinyl. In various embodiments, HET comprises dihydroimidazolyl, piperazinyl, diketopiperazinyl, $C_{2-5}$cyclic guanidinyl, $C_{2-5}$cyclic ureayl, or $C_{2-5}$cyclic thioureayl. In some cases, HET is

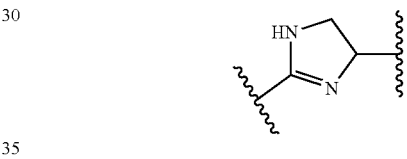

.

In various cases, $R^1$ is $C_{1-6}$alkyl. In some embodiments, $R^1$ is methyl, ethyl, propyl, isopropyl, butyl, 2-butyl, or isobutyl. In various embodiments, $R^1$ is methyl or isobutyl. In some embodiments, the $R^1$ group has R stereochemistry. In some cases, $R^1$ is $C_{0-3}$alkylene-$C_{3-7}$cycloalkyl. In various cases, the cycloalkyl comprises cyclobutyl, cyclopentyl, cyclohexyl, or cycloheptyl, such as $CH_2$-cyclohexyl. In some embodiments, $R^1$ is $C_{0-3}$alkylene-$C_{3-7}$heterocycloalkyl. In various embodiments, the $C_{3-7}$heterocycloalkyl comprises aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, piperazinyl, tetrahydropyranyl, tetrahydrothiopyranyl, pyranyl, thiopyranyl, or morpholinyl. In some cases, $R^1$ is $C_{0-3}$alkylene-$C_{6-10}$aryl. In various cases, the $C_{6-10}$aryl comprises phenyl. In some cases, $R^1$ is phenyl, benzyl, 4-fluorophenyl-methyl, or 4-ethoxybenzyl. In some embodiments, $R^1$ is $C_{0-3}$alkylene-$C_{2-6}$heteroaryl. In various embodiments, the $C_{2-6}$heteroaryl comprises pyrrolyl, pyrazolyl, imidazolyl, tetrazolyl, furanyl, thiophenyl, thiazolyl, oxazolyl, isooxazolyl, thiadiazolyl, oxadiazolyl, pyridinyl, pyrazinyl, pyrimidinyl, oxazolyl, or isoxazolyl. In some cases, $R^1$ is 3-methylpyridinyl. In some embodiments, the $R^1$ group has R stereochemistry. In some embodiments, $R^1$ is selected from the group consisting of methyl, isobutyl, and phenyl.

In some embodiments, $R^2$ is $C_{1-6}$alkyl. In various embodiments, $R^2$ is methyl, ethyl, propyl, isopropyl, butyl, s-butyl, isobutyl, t-butyl, pentyl, hexyl, heptyl, or 4-methylpentyl. In some cases, $R^2$ is 4-methylpentyl. In various embodiments, $R^2$ is $C_{1-3}$alkylene-$C_{3-7}$cycloalkyl. In some embodiments, the $C_{3-7}$cycloalkyl comprises cyclobutyl, cyclopentyl, cyclohexyl, or cycloheptyl. In some embodiments, $R^2$ is selected from the group consisting of

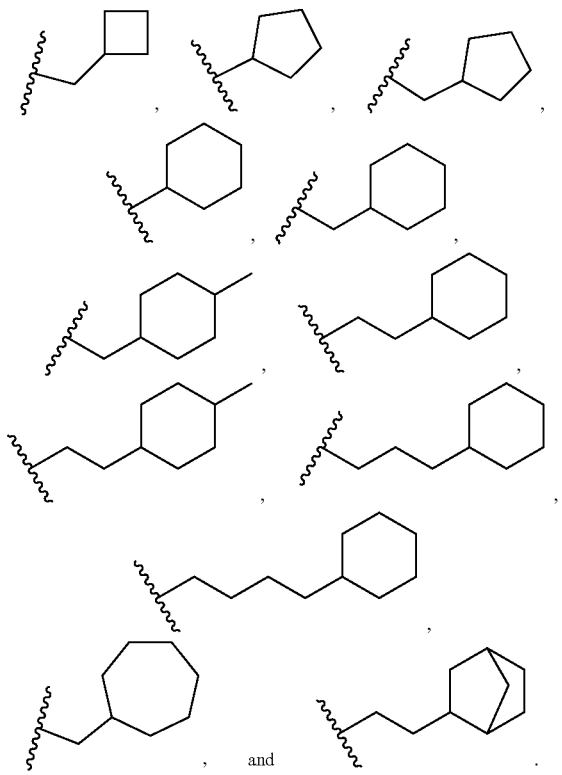

In various embodiments, $R^2$ is selected from the group consisting of

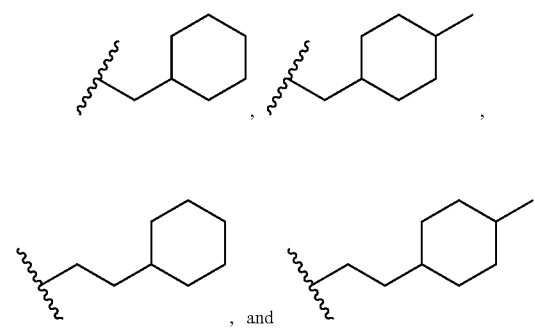

In some cases, $R^2$ is $C_{1-3}$alkylene-$C_{3-7}$heterocycloalkyl. In various cases, the $C_{3-7}$heterocycloalkyl comprises aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, piperazinyl, tetrahydropyranyl, tetrahydrothiopyranyl, pyranyl, thiopyranyl, or morpholinyl. In some embodiments, $R^2$ is $C_{1-3}$alkylene-$C_{6-10}$aryl or $C_{1-3}$alkylene-$C_{2-6}$heteroaryl. In various embodiments, the $C_{6-10}$aryl group comprises phenyl and the $C_{2-6}$heteroaryl comprises pyrrolyl, pyrazolyl, imidazolyl, tetrazolyl, furanyl, thiophenyl, thiazolyl, oxazolyl, isooxazolyl, thiadiazolyl, oxadiazolyl, pyridinyl, pyrazinyl, pyrimidinyl, oxazolyl, or isoxazolyl. In some cases, $R^2$ is

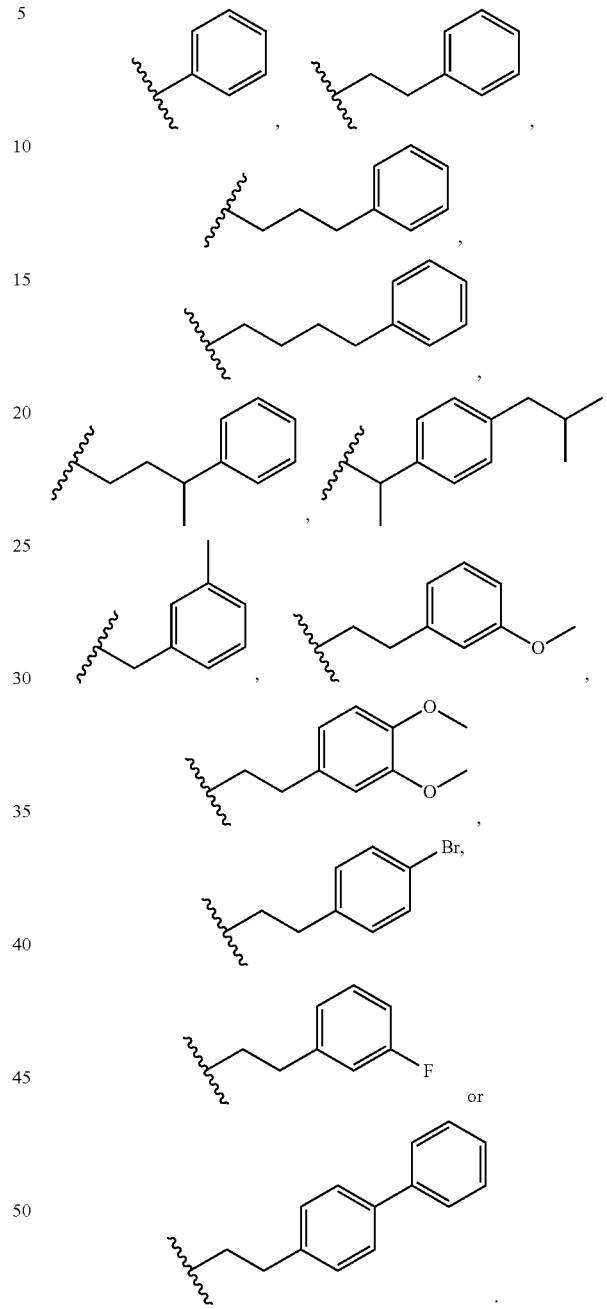

In some embodiments, $R^2$ is selected from the group consisting of 4-methylpentyl, $CH_2CH_2$-cyclohexyl, and $CH_2$-4-methylcyclohexyl.

In various cases, $R^3$ is $C_{1-6}$alkyl. In some embodiments, $R^3$ is methyl, ethyl, propyl, isopropyl, butyl, s-butyl, isobutyl, t-butyl, 2-methylbutyl, 3-methylbutyl, 4-methylpentyl. In various embodiments, $R^3$ is s-butyl. In some embodiments, $R^3$ is 2-methylbutyl. In some cases, $R^3$ is $C_{0-3}$alkylene-$C_{3-7}$cycloalkyl. In various cases, the $C_{3-7}$cycloalkyl comprises cyclopentyl or cyclohexyl. In some embodiments, $R^3$ is

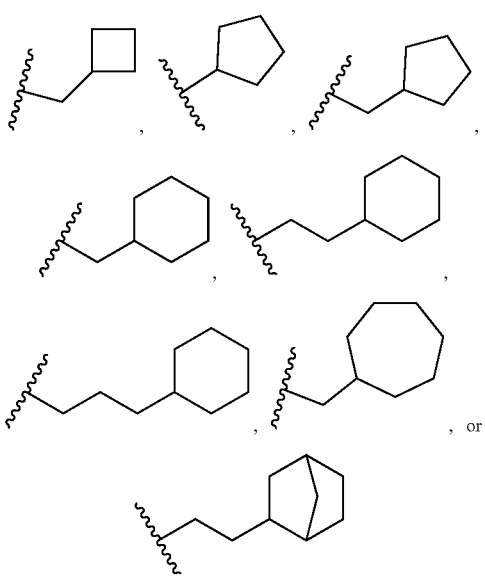

In various cases, R³ is

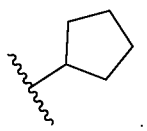

In some embodiments, R³ is C₀₋₃alkylene-C₃₋₇heterocycloalkyl. In some embodiments, C₃₋₇heterocycloalkyl comprises aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, piperazinyl, tetrahydropyranyl, tetrahydrothiopyranyl, pyranyl, thiopyranyl, or morpholinyl. In various embodiments, R³ is C₁₋₃alkylene-C₆₋₁₀aryl or C₁₋₃alkylene-C₂₋₆heteroaryl. In some cases, the C₆₋₁₀aryl group comprises phenyl and the C₂₋₆heteroaryl comprises pyrrolyl, pyrazolyl, imidazolyl, tetrazolyl, furanyl, thiophenyl, thiazolyl, oxazolyl, isooxazolyl, thiadiazolyl, oxadiazolyl, pyridinyl, pyrazinyl, pyrimidinyl, oxazolyl, or isoxazolyl. In some embodiments, R³ is

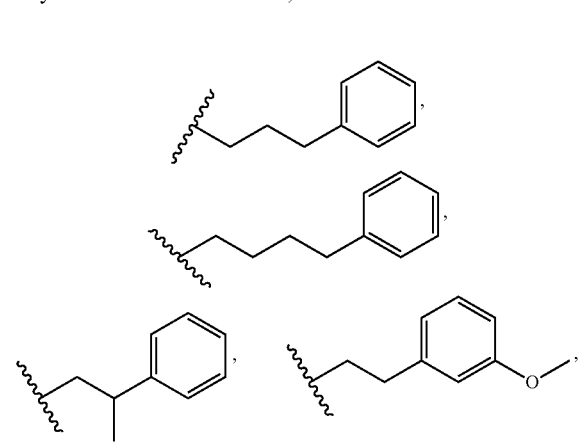

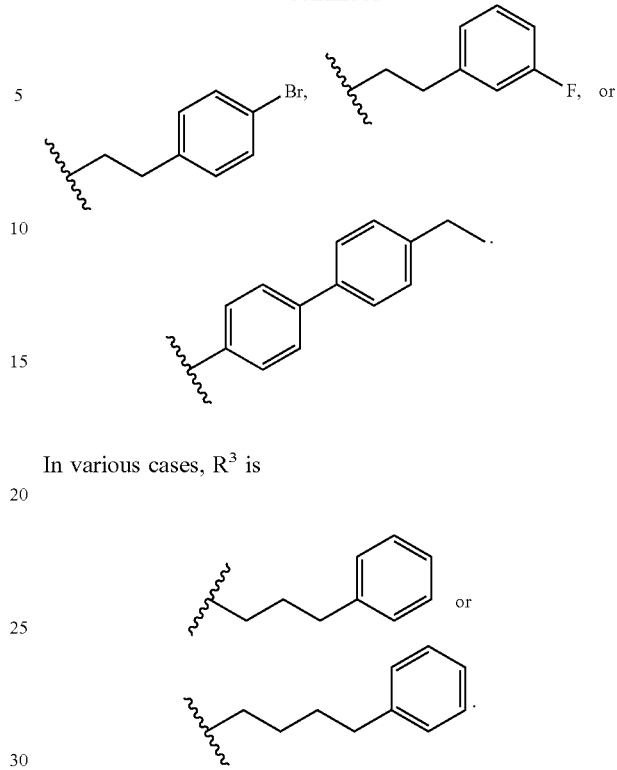

In various cases, R³ is

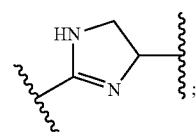 [SMILES: *C1=NC(*)CN1]

In some embodiments, R³ is selected from the group consisting of s-butyl, cyclopentyl, and propylbenzene.

In some embodiments, m is 4; n is 1; X is S; HET is

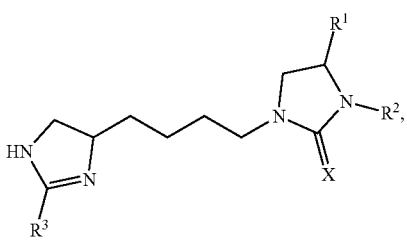

R¹ is C₁₋₆alkyl or C₀₋₃alkylene-C₆₋₁₀aryl; R² is C₁₋₃alkylene-C₃₋₇cycloalkyl, and R³ is C₁₋₆alkyl, C₀₋₃alkylene-C₃₋₇cycloalkyl, or C₁₋₃alkylene-C₆₋₁₀aryl. In some cases, the compound of Formula (I) has a structure:

wherein R¹ is C₁₋₆alkyl or C₀₋₃alkylene-C₆₋₁₀aryl; R² is C₁₋₃alkylene-C₃₋₇cycloalkyl, and R³ is C₁₋₈alkyl, C₀₋₃alkylene-C₃₋₇cycloalkyl, or C₁₋₃alkylene-C₆₋₁₀aryl. In various cases, m is 4; n is 1; X is X; HET is dihydroimidazole, R¹ is methyl, isobutyl, or phenyl; R² is 4-methylpentyl, CH₂CH₂-cyclohexyl, or CH₂-4-methylcyclohexyl; and R³ is s-butyl, cyclopentyl, or (CH₂)₃-Ph. As referred to herein, "cyclohexyl-ethyl" is 4-methyl-1-cyclohexylmethyl is

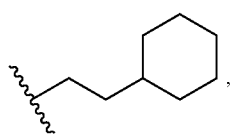 [SMILES: *CCC1CCCCC1],

"butylbenzene" is

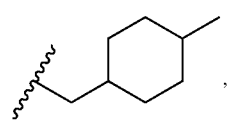 [SMILES: *CC1CCC(C)CC1],

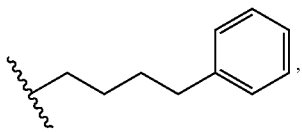 [SMILES: *CCCCc1ccccc1],

"cyclopentylmethyl" is

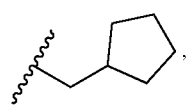,

In some cases, the compounds of the disclosure include those listed in Table A, or a pharmaceutically acceptable salt thereof:

TABLE A

| Compound # | R$^1$ | R$^2$ | R$^3$ |
|---|---|---|---|
| A1  | methyl   | 4-methylpentyl            | s-butyl      |
| A2  | methyl   | 4-methylpentyl            | cyclopentyl  |
| A3  | methyl   | 4-methylpentyl            | (CH$_2$)$_3$—Ph |
| A4  | methyl   | CH$_2$CH$_2$-cyclohexyl   | s-butyl      |
| A5  | methyl   | CH$_2$CH$_2$-cyclohexyl   | cyclopentyl  |
| A6  | methyl   | CH$_2$CH$_2$-cyclohexyl   | (CH$_2$)$_3$—Ph |
| A7  | methyl   | CH$_2$-4-methylcyclohexyl | s-butyl      |
| A8  | methyl   | CH$_2$-4-methylcyclohexyl | cyclopentyl  |
| A9  | methyl   | CH$_2$-4-methylcyclohexyl | (CH$_2$)$_3$—Ph |
| A10 | isobutyl | 4-methylpentyl            | s-butyl      |
| A11 | isobutyl | 4-methylpentyl            | cyclopentyl  |
| A12 | isobutyl | 4-methylpentyl            | (CH$_2$)$_3$—Ph |
| A13 | isobutyl | CH$_2$CH$_2$-cyclohexyl   | s-butyl      |
| A14 | isobutyl | CH$_2$CH$_2$-cyclohexyl   | cyclopentyl  |
| A15 | isobutyl | CH$_2$CH$_2$-cyclohexyl   | (CH$_2$)$_3$—Ph |
| A16 | isobutyl | CH$_2$-4-methylcyclohexyl | s-butyl      |
| A17 | isobutyl | CH$_2$-4-methylcyclohexyl | cyclopentyl  |
| A18 | isobutyl | CH$_2$-4-methylcyclohexyl | (CH$_2$)$_3$—Ph |
| A19 | phenyl   | 4-methylpentyl            | s-butyl      |
| A20 | phenyl   | 4-methylpentyl            | cyclopentyl  |

TABLE A-continued

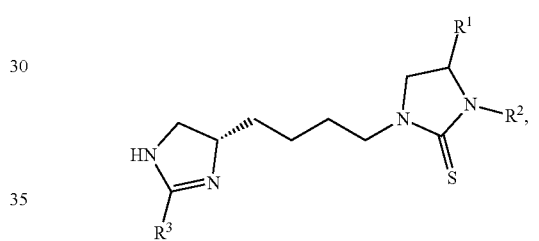

| Compound # | R$^1$ | R$^2$ | R$^3$ |
|---|---|---|---|
| A21 | phenyl | 4-methylpentyl            | (CH$_2$)$_3$—Ph |
| A22 | phenyl | CH$_2$CH$_2$-cyclohexyl   | s-butyl      |
| A23 | phenyl | CH$_2$CH$_2$-cyclohexyl   | cyclopentyl  |
| A24 | phenyl | CH$_2$CH$_2$-cyclohexyl   | (CH$_2$)$_3$—Ph |
| A25 | phenyl | CH$_2$-4-methylcyclohexyl | s-butyll     |
| A26 | phenyl | CH$_2$-4-methylcyclohexyl | cyclopentyl  |
| A27 | phenyl | CH$_2$-4-methylcyclohexyl | (CH$_2$)$_3$—Ph |

In some cases, the compounds in Table A, exhibit the following stereochemistry:

In various cases, the R$^1$ groups in Table A exhibit R stereochemistry. In some embodiments, specifically contemplated compounds of the disclosure include:

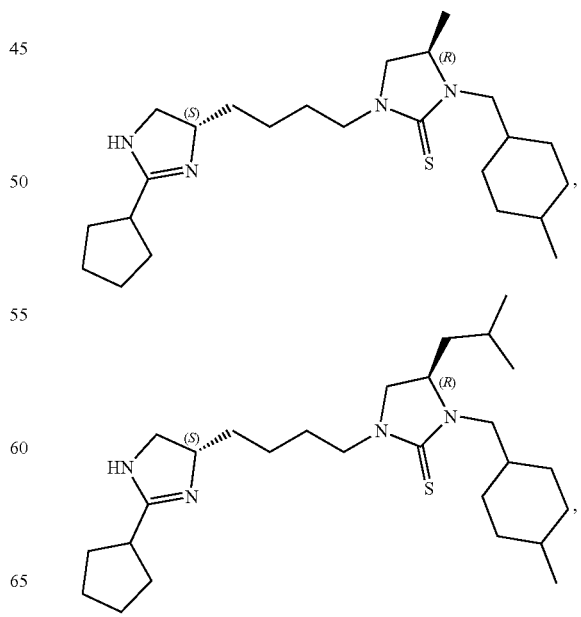

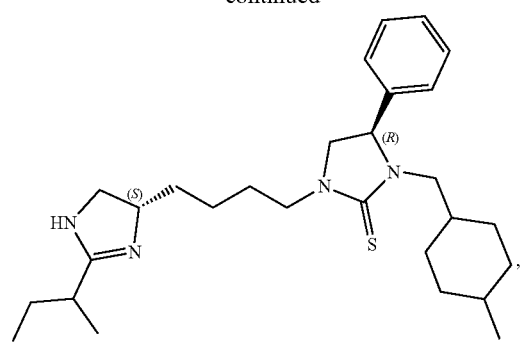

,

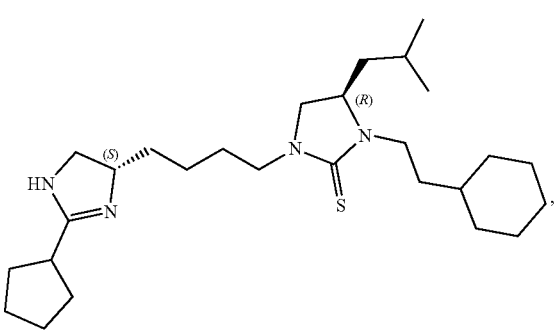

,

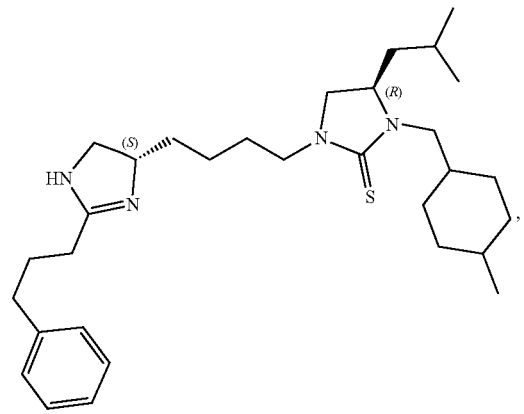

,

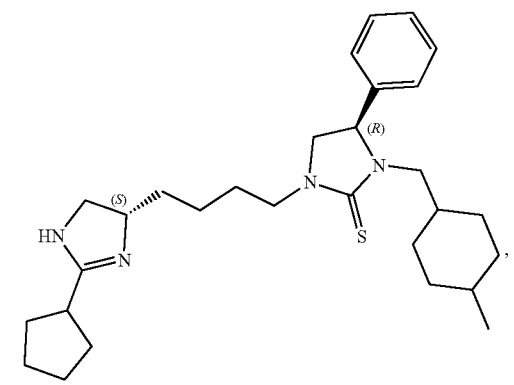

,

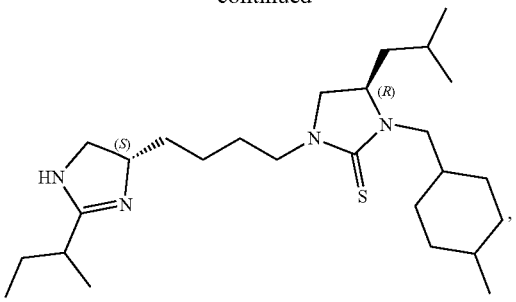

,

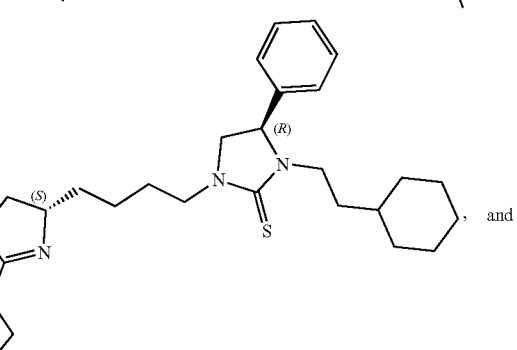

,

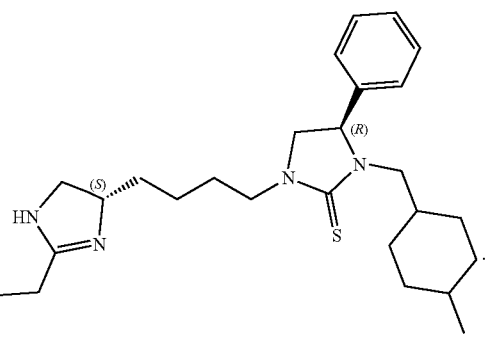 and

.

The chemical structures having one or more stereocenters depicted with dashed and bold bonds (i.e., ⋯⋯ and ▬) are meant to indicate absolute stereochemistry of the stereocenter(s) present in the chemical structure. Bonds symbolized by a simple line do not indicate a stereo-preference. Unless otherwise indicated to the contrary, chemical structures that include one or more stereocenters which are illustrated herein without indicating absolute or relative stereochemistry, encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Synthesis of Compounds

Compounds disclosed herein can be synthesized by any means available to the synthetic organic chemist. Guidance for the synthesis of compounds is shown in the Examples section.

In some cases, a compound of Formula (I) can be prepared by solid phase synthesis with Boc chemistry, using standard coupling chemistry, as shown according to Scheme 1, below.

Scheme 1

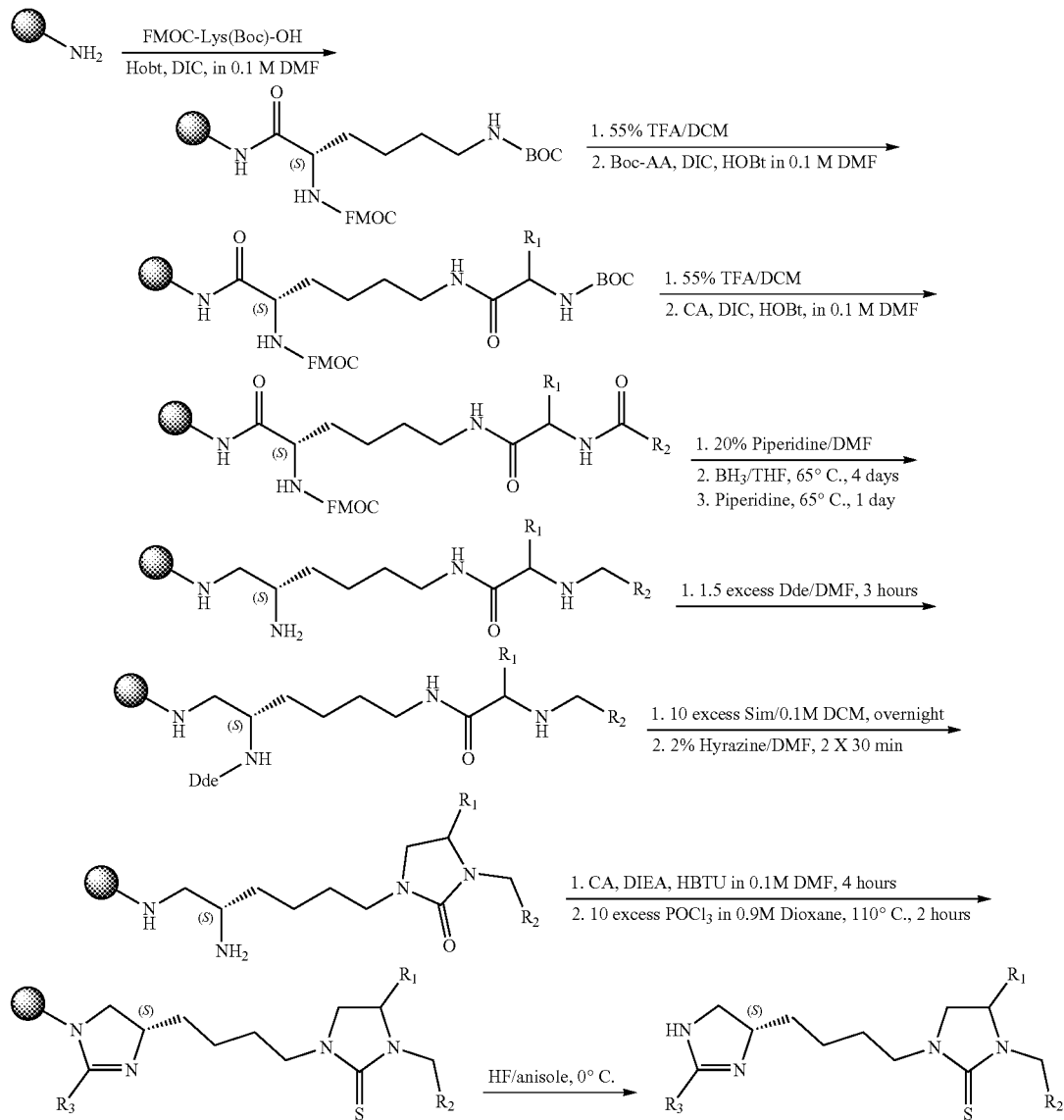

For example, a Boc-protected amino acid having aliphatic amino side chain with the desired number of carbon atoms (m=3, 4, or 5) can be coupled to an appropriate solid phase resin. The resulting compound can be coupled to an appropriate Boc-protected amino acid having a side chain desired for $R^1$. The resulting compound can be coupled to an appropriate Boc-protected amino acid having a side chain desired for $R^2$. The imidazolidine-2-thionyl group can be formed by reacting the resulting compound with hydrazine. Next, the dihydroimidazolyl moiety having an appropriate $R^3$ group can be formed by reacting the imidazolidine-2-thionyl compound with the appropriate carboxylic acid and subsequent cyclization with $POCl_3$. Finally, the desired compound can be cleaved from the resin by treatment with HF.

Pharmaceutical Formulations and Administration

Further provided are pharmaceutical compositions comprising a compound as described herein (e.g., a compound of Formula (I), listed in Table A, or pharmaceutically acceptable salt thereof) and a pharmaceutically acceptable carrier.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66:1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Actual dosage levels of the active ingredients in the pharmaceutical compositions provided herein may be varied so as to obtain "therapeutically effective amount," which is an amount of the active ingredient effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds disclosed herein can induce neurite outgrowth. As used herein, the term "neurite outgrowth" refers to a process wherein developing neurons produce new projections. In some embodiments, the compounds described herein (e.g., the compounds of Formula (I), the compounds, in Table A, and pharmaceutically acceptable salts thereof) can increase neurite growth length by at least 50%, at least 75%, at least 100%, at least 125%, at least 150%, at least 175%, at least 200%, at least 225%, at least 250%, or at least 300%. In various embodiments, the compounds disclosed herein exhibit nanomolar potency in hippocampal neurons. In some embodiments, the compounds disclosed herein (e.g., the compounds of Formula (I), the compounds, in Table A, and pharmaceutically acceptable salts thereof) exhibit a 200% effective dose of up to 5 nM, up to 10 nM, up to 15 nM, up to 20 nM, up to 30 nM, up to 50 nM, up to 75 nM, up to 100 nM, up to 125 nM, or up to 150 nM. In some cases, the compounds disclosed herein (e.g., the compounds of Formula (I), the compounds, in Table A, and pharmaceutically acceptable salts thereof) exhibit a 300% effective dose of up to 25 nM, up to 50 nM, up to 75 nM, up to 100 nM, up to 200 nM, up to 300 nM, up to 400 nM, or up to 500 nM.

In some cases, the compounds disclosed herein (e.g., the compounds of Formula (I), the compounds, in Table A, and pharmaceutically acceptable salts thereof) can treat a CNS disorder associated with neuronal and/or axonal damage. As used herein, the term "CNS disorder associated with neuronal and/or axonal damage" relates to a disease or condition that affects the structure of function of the brain or spinal cord, and that results from an interruption in one or more connections between neurons and/or axons within neuron and/or axon networks and nerve tissue. For example, the compounds disclosed herein (e.g., the compounds of Formula (I), the compounds, in Table A, and pharmaceutically acceptable salts thereof) can treat a CNS disorder such as paralysis, spinal cord injury, optic nerve injury, glaucoma, multiple sclerosis, traumatic brain injury, diffuse axonal injury, stroke, or a degenerative disease (such as Parkinson's disease).

In some cases, the compounds disclosed herein (e.g., the compounds of Formula (I), the compounds, in Table A, and pharmaceutically acceptable salts thereof) can treat a peripheral nervous system ("PNS") disorder associated with neuronal and/or axonal damage. As used herein, the term "PNS disorder associated with neuronal and/or axonal damage" relates to a disease or condition that affects the structure of function of the nervous system outside of the brain or spinal cord, and that results from an interruption in one or more connections between neurons and/or axons within neuron and/or axon networks and nerve tissue. In some cases, the PNS disorder is peripheral nerve trauma, repetitive stress, amyotropic lateral sclerosis ("ALS"), erectile dysfunction, a disorder associated with an organ transplant, neurofibromatosis, blood vessel disease, diabetes, an autoimmune disorder, a disorder associated with chemical toxicity, or kidney disease.

In some cases, the compounds disclosed herein (e.g., the compounds of Formula (I), the compounds, in Table A, and pharmaceutically acceptable salts thereof) can treat nerve degeneration in a subject undergoing cancer therapy. As used herein, the term "nerve degeneration" refers to the loss of functional activity and/or trophic degeneration of nerve axons and/or their terminal arborizations.

The compounds disclosed herein (e.g., the compounds of Formula (I), the compounds, in Table A, and pharmaceutically acceptable salts thereof) can be useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) memory loss, and (v) psychiatric disorders. As used herein, the term "neurodegenerative disease" refers to a disease or condition that primarily affects the neurons in the brain.

Examples of neurodegenerative diseases and conditions that can be prevented or treated by promoting neurite outgrowth according to the invention include amyotrophic lateral sclerosis ("ALS"), trigeminal neuralgia, glossopharyngeal neuralgia, Bell's palsy, myasthenia gravis, muscular dystrophy, progressive muscular atrophy, primary lateral sclerosis ("PLS"), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson-plus syndromes (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease ("CMT"; also known as Hereditary Motor and Sensory Neuropathy ("HMSN"), Hereditary Sensorimotor Neuropathy ("HSMN"), and Peroneal Muscular Atrophy), prion disease (e.g., Creutzfeldt-Jakob disease, Gerstmann-Straussler-Scheinker syndrome ("GSS"), fatal familial insomnia ("FFI"), and bovine spongiform encephalopathy (BSE, commonly known as mad cow disease)), Pick's disease, epilepsy, and AIDS demential complex (also known as HIV dementia, HIV encephalopathy, and HIV-associated dementia).

Certain diseases and conditions having primary effects outside of the nervous system can lead to damage to the nervous system, which can be treated using compounds as disclosed herein. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the compounds disclosed herein (e.g., the compounds of Formula (I), the compounds, in Table A, and pharmaceutically acceptable salts thereof) can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The compounds disclosed herein (e.g., the compounds of Formula (I), the compounds, in Table A, and pharmaceutically acceptable salts thereof) can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), chemical trauma (e.g., due to chemotherapy as a cancer treatment) as well as damage to the central nervous system due to, for example, stroke or intracranial hemorrhage (such as cerebral hemorrhage).

Further, the compounds disclosed herein (e.g., the compounds of Formula (I), the compounds, in Table A, and pharmaceutically acceptable salts thereof) can be used in the prevention or treatment of memory loss such as, for example, age-related memory loss. Types of memory that can be affected by loss include episodic memory, semantic memory, short-term memory, and long-term memory. Examples of diseases and conditions associated with memory loss include mild cognitive impairment, Alzheimer's disease, Parkinson's disease, Huntington's disease, chemotherapy, stress, stroke, and traumatic brain injury (e.g., concussion).

The compounds disclosed herein (e.g., the compounds of Formula (I), the compounds, in Table A, and pharmaceutically acceptable salts thereof) can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

Further guidance for using compounds and compositions described herein (e.g., a compound of Formula (I) or a compound listed in Table A, or a pharmaceutically acceptable salt of the foregoing) for inhibiting protein secretion can be found in the Examples section, below.

OTHER EMBODIMENTS

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

Materials and Methods

The $^1$H and $^{13}$C NMR spectra were obtained utilizing the Bruker 400' Ascend (400 and 101 MHz, respectively)). NMR chemical shifts were reported in δ (ppm) using the δ 2.50 signal of DMSO-d6 as an internal standard. Confirmation of the desired product was obtained by reverse phase LCMS analysis using a Shimadzu 2010 LCMS system, consisting of a LC-20AD binary solvent pump, a DGU-20A degasser unit, a CTO-20A column oven, SIL-20A HT auto sampler, and SPD-M20A diode array set to scan 190-600 nm. Separation was achieved using a Phenomenex Gemini C18 column (5 μm, 50 mm×4.6 mm i.d.) protected with a Phenomenex C18 column guard column (5 μm, 4×3.0 mm i.d.), mobile (A) Water with 0.1% Formic acid and mobile phase (B) acetonitrile with 0.1% formic acid. A gradient of 5-95% mobile phase B over 6 minutes was run.

Synthetic Procedures

The compounds were synthesized as described in Scheme 1, described above, using standard Boc chemistry. The solid phase synthesis was performed using the "tea-bag" methodology. The desired product was cleaved from the solid support resin and extracted using 95% acetic acid. Samples were then repeatedly frozen and lyophilized in 50% acetonitrile and water three times prior to analysis.

During purification, the peak corresponding to the desired product with calculated m/z was isolated and concentrated. Compounds were purified using a Shimadzu Prominence preparative HPLC system consisting of LC-8A binary solvent pumps, a SCL-10A system controller, a SIL-10AP auto sampler, a FRC-10A fraction collector, and a Shimadzu SPD-20A UV detector. The wavelength was set to 214 nm.

Chromatographic separations were obtained using a Phenomenex Gemini NX-C18 preparative column (5 μm, 150 mm×21.2 mm i.d.). The column was protected by a Phenomenex C18 column guard (5 μm, 15 mm×21.2 mm i.d.). Prominence prep software was used for detection and collection parameters. The mobile phases for HPLC purification were HPLC grade obtained from Sigma-Aldrich and Fisher Scientific. The mobile phase A consisted of water with 0.1% trifluoroacetic acid and mobile phase B consisted of acetonitrile with 0.1% trifluoroacetic acid. Initial setting was set to 2% Mobile phase B and was gradually increased over time to achieve ideal separation for each compound.

Preparation of Compound A8: (R)-1-(4-((S)-2-cyclopentyl-4,5-dihydro-1H-imidazol-4-yl)butyl)-4-methyl-3-((4-methylcyclohexyl)methyl)imidazolidine-2-thione Compound A8 was synthesized with Boc-D-alanine reagent used for $R^1$, 4-methyl-1-cyclohexanecarboxylic acid for $R^2$, and cyclopentanecarboxylic acid for $R^3$. LCMS (ESI+) m/z calculated for $C_{24}H_{42}N_4S$ [M+H]+: 419.31 mw found 419.25. $^1$H NMR (400 MHz, D$_2$O) δ ppm 0.81-1.03 (m, 3H) 1.18 (br. s., 3H) 1.31 (br. s., 3H) 1.38 (br.s., 2H) 1.45 (br. s., 1H) 1.50-1.74 (m, 9H) 1.88 (br. s., 1H) 1.98 (br. s., 2H) 2.92 (br. s., 1H) 3.03 (d, J=13.69 Hz, 1H) 3.12 (br. s., 1H) 3.33-3.60 (m, 8H) 3.60-3.76 (m, 2H) 3.77-4.03 (m, 2H) 4.20 (br. s., 1H) 9.92 (br. s., 1H) 10.03 (br. s., 1H).

Preparation of Compound A14: (R)-3-(2-cyclohexylethyl)-1-(4-((S)-2-cyclopentyl-4,5-dihydro-1H-imidazol-4-yl)butyl)-4-isobutylimidazolidine-2-thione Compound A14 was synthesized with Boc-D-Leucine reagent used for $R^1$, cyclohexylacetic acid for $R^2$, and cyclopentanecarboxylic acid for $R^3$. LCMS (ESI+) m/z calculated for $C_{27}H_{48}N_4S$ [M+H]+: 461 mw found 461. $^1$H NMR (400 MHz, D$_2$O) 6 ppm 0.86-1.01 (m, 6H) 1.20 (d, J=19.07 Hz, 4H) 1.31 (br. s., 3H) 1.43 (br. s., 1H) 1.51-1.78 (m, 14H) 1.98 (br. s., 2H) 2.82-3.05 (m, 1H) 3.18 (br. s., 2H) 3.38 (br. s., 5H) 3.51 (br. s., 3H) 3.69 (br. s., 1H) 3.75-3.85 (m, 1H) 3.85-4.05 (m, 2H) 4.20 (br. s., 1H) 9.87 (br. s., 1H) 9.98 (br. s., 1H).

Preparation of Compound A16: (4R)-1-(4-((4S)-2-(sec-butyl)-4,5-dihydro-1H-imidazol-4-yl)butyl)-4-isobutyl-3-((4-methylcyclohexyl)methyl)imidazolidine-2-thione Compound A16 was synthesized using Boc-D-Leucine for $R^1$, 4-methyl-1-cyclohexanecarboxylic acid for $R^2$, and (+/−)-2-methylbutyric acid for $R^3$. LCMS (ESI+) m/z calculated for $C_{26}H_{48}N_4S$ [M+H]+: 449 mw found 449. $^1$H NMR (400 MHz, D$_2$O) δ ppm 0.80-0.99 (m, 15H) 1.18 (br. s., 3H) 1.30 (br. s., 3H) 1.37 (br. s., 2H) 1.45 (br. s., 2H) 1.58 (br. s., 8H) 1.85 (br. s., 1H) 2.60 (br. s., 2H) 2.96-3.06 (m, 1H) 3.20 (br. s., 1H) 3.29 (br. s., 6H) 3.52 (br. s., 2H) 3.68 (br. s., 1H) 3.78 (br. s., 1H) 3.87-3.97 (m, 1H) 9.90 (br. s., 1H) 10.01 (br. s., 1H).

Preparation of Compound A17: (R)-1-(4-((S)-2-cyclopentyl-4,5-dihydro-1H-imidazol-4-yl)butyl)-4-isobutyl-3-((4-methylcyclohexyl)methyl)imidazolidine-2-thione Compound A17 was synthesized using Boc-D-Leucine for $R^1$, 4-methyl-1-cyclohexanecarboxylic acid for $R^2$, and cyclopentanecarboxylic acid for $R^3$. LCMS (ESI+) m/z calculated for $C_{27}H_{48}N_4S$ [M+H]+: 461 mw found 461. $^1$H NMR (400 MHz, $D_2O$) δ ppm 0.91 (br. s., 9H) 1.31 (br. s., 4H) 1.38 (br. s., 2H) 1.46 (br. s., 2H) 1.53-1.73 (m, 10H) 1.86 (br.s., 2H) 1.98 (br. s., 2H) 2.93 (br. s., 1H) 3.01 (d, J=13.45 Hz, 1H) 3.21 (br. s., 1H) 3.35 (br. s., 6H) 3.50 (br. s., 3H) 3.69 (br. s., 1H) 3.79 (br.s., 1H) 3.91 (t, J=10.58 Hz, 1H) 3.96-4.09 (m, 1H) 4.20 (br. s., 1H) 9.88 (br. s., 1H) 9.99 (br. s., 1H).

Preparation of Compound A18: (R)-4-isobutyl-3-((4-methylcyclohexyl)methyl)-1-(4-((S)-2-(3-phenylpropyl)-4,5-dihydro-1H-imidazol-4-yl)butyl)imidazolidine-2-thione Compound A18 was synthesized using Boc-D-Leucine for $R^1$, 4-methyl-1-cyclohexanecarboxylic acid for $R^2$, and 4-phenylbutyric acid for $R^3$. LCMS (ESI+) m/z calculated for $C_{31}H_{50}N_4S$ [M H]+: 511 mw found 511. $^1$H NMR (400 MHz, $D_2O$) δ ppm 0.81-1.01 (m, 9H) 1.18-1.34 (m, 4H) 1.38 (br. s., 2H) 1.46 (br. s., 1H) 1.51-1.69 (m, 6H) 1.72-1.98 (m, 2H) 2.52-2.68 (m, 3H) 2.94-3.11 (m, 1H) 3.20 (br. s., 1H) 3.32-3.50 (m, 10H) 3.53 (br. s., 1H) 3.69 (br. s., 1H) 3.79 (br. s., 1H) 3.89 (t, J=9.78 Hz, 1H) 4.01 (br. s., 1H) 4.17 (br. s., 1H) 7.23 (br. s., 2H) 7.28-7.35 (m, 1H) 9.93 (br. s., 1H) 10.07 (br. s., 1H).

Preparation of Compound A23: (R)-3-(2-cyclohexylethyl)-1-(4-((S)-2-cyclopentyl-4,5-dihydro-1H-imidazol-4-yl)butyl)-4-phenylimidazolidine-2-thione Compound A23 was synthesized using Boc-D-phenylglycine for $R^1$, cyclohexylacetic acid for $R^2$, and cyclopentanecarboxylic acid for $R^3$. LCMS (ESI+) m/z calculated for $C_{29}H_{44}N_4S$ [M+H]+: 481 mw found 481. NMR (400 MHz, $D_2O$) δ ppm 0.71-0.96 (m, 2H) 1.11 (br. s., 3H) 1.24 (br. s., 1H) 1.32 (br. s., 2H) 1.52-1.76 (m, 11H) 1.98 (br. s., 2H) 2.80 (br. s., 1H) 2.92 (br. s., 1H) 3.33 (br. s., 8H) 3.41 (br. s., 1H) 3.45-3.57 (m, 2H) 3.59-3.77 (m, 1H) 3.80-4.03 (m, 2H) 4.21 (br. s., 1H) 4.91 (br. s., 1H) 7.29 (br. s., 1H) 7.34-7.47 (m, 2H) 9.86 (br. s., 1H) 9.97 (br. s., 1H).

Preparation of Compound A25: (4R)-1-(4-((4S)-2-(sec-butyl)-4,5-dihydro-1H-imidazol-4-yl)butyl)-3-((4-methylcyclohexyl)methyl)-4-phenylimidazolidine-2-thione Compound A25 was synthesized using Boc-D-phenylglycine reagent for $R^1$, 4-methyl-1-cyclohexanecarboxylic acid for $R^2$, and (+/−)-2-methylbutyric acid for $R^3$. LCMS (ESI+) m/z calculated for $C_{28}H_{44}N_4S$ [M+H]+: 469 mw found 469. $^1$H NMR (400 MHz, $D_2O$) δ ppm 0.86 (br. s., 5H) 1.19 (br. s., 4H) 1.31 (br.s., 5H) 1.48-1.69 (m, 6H) 1.78 (br. s., 1H) 2.52-2.66 (m, 4H) 3.39 (br. s., 5H) 3.50 (br. s., 2H) 3.72 (d, J=6.60 Hz, 1H) 3.85-4.08 (m, 2H) 4.22 (br. s., 1H) 4.93 (br. s., 1H) 7.24 (br. s., 2H) 7.34-7.49 (m, 1H) 9.93 (br. s., 1H) 10.04 (br. s., 1H).

Preparation of Compound A26: (R)-1-(4-((S)-2-cyclopentyl-4,5-dihydro-1H-imidazol-4-yl)butyl)-3-((4-methylcyclohexyl)methyl)-4-phenylimidazolidine-2-thione Compound A26 was synthesized using Boc-D-phenylglycine for $R^1$ reagent, 4-methyl-1-cyclohexanecarboxylic acid for $R^2$, and cyclopentanecarboxylic acid for $R^3$. LCMS (ESI+) m/z calculated for $C_{29}H_{44}N_4S$ [M+H]+: 481 mw found 481. $^1$H NMR (400 MHz, $D_2O$) δ ppm 0.84 (br. s., 3H) 1.14 (br. s., 1H) 1.22-1.40 (m, 7H) 1.49-1.69 (m, 8H), 1.76 (br. s., 2H) 1.97 (br. s., 2H) 2.52-2.67 (m, 1H) 2.85-2.97 (m, 1H) 3.45 (br. s., 8H) 3.71 (d, J=6.24 Hz, 1H) 3.82-4.06 (m, 2H) 4.19 (br. s., 1H) 4.92 (br. s., 1H) 7.22 (br. s., 2H) 7.32-7.45 (m, 2H) 9.88 (br. s., 1H).

Preparation of Compound A27: (R)-3-((4-methylcyclohexyl)methyl)-4-phenyl-1-(4-((S)-2-(3-phenylpropyl)-4,5-dihydro-1H-imidazol-4-yl)butyl)imidazolidine-2-thione Compound A27 was synthesized using Boc-D-phenylglycine $R^1$, 4-methyl-1-cyclohexanecarboxylic acid for $R^2$, and 4-phenylbutyric acid for $R^3$. LCMS (ESI+) m/z calculated for $C_{33}H_{46}N_4S$ [M+H]+: 531 mw found 531. NMR (400 MHz, $D_2O$) δ ppm 0.86 (br. s., 3H) 1.15 (br. s., 1H) 1.31 (br. s., 6H) 1.46-1.67 (m, 4H) 1.78 (br. s., 1H) 1.85-2.00 (m, 2H) 2.52-2.69 (m, 4H) 3.30-3.55 (m, 9H) 3.71 (d, J=6.36 Hz, 1H) 3.81-3.95 (m, 1H) 3.95-4.07 (m, 1H) 4.17 (br. s., 1H) 4.92 (br. s., 1H) 7.23 (br. s., 4H) 7.27-7.46 (m, 4H) 9.98 (br. s., 1H) 10.11 (br. s., 1H).

Preparation of Compound A1: (4R)-1-(4-((4S)-2-(sec-butyl)-4,5-dihydro-1H-imidazol-4-yl)butyl)-4-methyl-3-(4-methylpentyl)imidazolidine-2-thione Compound A1 was synthesized with Boc-D-alanine reagent used for $R^1$, 4-methylvaleric acid for $R^2$, and (+/−)-2-methylbutyric acid for $R^3$.

Preparation of Compound A2: (R)-1-(4-((S)-2-cyclopentyl-4,5-dihydro-1H-imidazol-4-yl)butyl)-4-methyl-3-(4-methylpentyl)imidazolidine-2-thione Compound A2 was synthesized with Boc-D-alanine reagent used for $R^1$, 4-methylvaleric acid for $R^2$, and cyclopentanecarboxylic acid for $R^3$.

Preparation of Compound A3: (R)-4-methyl-3-(4-methylpentyl)-1-(4-((S)-2-(3-phenylpropyl)-4,5-dihydro-1H-imidazol-4-yl)butyl)imidazolidine-2-thione Compound A3 was synthesized with Boc-D-alanine reagent used for $R^1$, 4-methylvaleric acid for $R^2$, and 4-phenylbutyric acid for $R^3$.

Preparation of Compound A4: (4R)-1-(4-((4S)-2-(sec-butyl)-4,5-dihydro-1H-imidazol-4-yl)butyl)-3-(2-cyclohexylethyl)-4-methylimidazolidine-2-thione Compound A4 was synthesized with Boc-D-alanine reagent used for $R^1$, cyclohexylacetic acid for $R^2$, and (+/−)-2-methylbutyric acid for $R^3$.

Preparation of Compound A5: (R)-3-(2-cyclohexylethyl)-1-(4-((S)-2-cyclopentyl-4,5-dihydro-1H-imidazol-4-yl)butyl)-4-methylimidazolidine-2-thione Compound A5 was synthesized with Boc-D-alanine reagent used for $R^1$, cyclohexylacetic acid for $R^2$, and cyclopentanecarboxylic acid for $R^3$.

Preparation of Compound A6: (R)-3-(2-cyclohexyl-ethyl)-4-methyl-1-(4-((S)-2-(3-phenylpropyl)-4,5-dihydro-1H-imidazol-4-yl)butyl)imidazolidine-2-thione Compound A6 was synthesized with Boc-D-alanine reagent used for $R^1$, cyclohexylacetic acid for $R^2$, and 4-phenylbutyric acid for $R^3$.

Preparation of Compound A7: (4R)-1-(4-((4S)-2-(sec-butyl)-4,5-dihydro-1H-imidazol-4-yl)butyl)-4-methyl-3-((4-methylcyclohexyl)methyl)imidazolidine-2-thione Compound A7 was synthesized with Boc-D-alanine reagent used for $R^1$, 4-methyl-1-cyclohexanecarboxylic acid for $R^2$, and (+/−)-2-methylbutyric acid for $R^3$.

Preparation of Compound A9: (R)-4-methyl-3-((4-methylcyclohexyl)methyl)-1-(4-((S)-2-(3-phenylpropyl)-4,5-dihydro-1H-imidazol-4-yl)butyl)imidazolidine-2-thione Compound A9 was synthesized with Boc-D-alanine reagent used for $R^1$, 4-methyl-1-cyclohexanecarboxylic acid for $R^2$, and 4-phenylbutyric acid for $R^3$.

Preparation of Compound A10: (4R)-1-(4-((4S)-2-(sec-butyl)-4,5-dihydro-1H-imidazol-4-yl)butyl)-4-isobutyl-3-(4-methylpentyl)imidazolidine-2-thione Compound A10 was synthesized with Boc-D-leucine reagent used for $R^1$, 4-methylvaleric acid for $R^2$, and (+/−)-2-methylbutyric acid for $R^3$.

Preparation of Compound A11: (R)-1-(4-((S)-2-cyclopentyl-4,5-dihydro-1H-imidazol-4-yl)butyl)-4-isobutyl-3-(4-methylpentyl)imidazolidine-2-thione Compound A11 was synthesized with Boc-D-leucine reagent used for $R^1$, 4-methylvaleric acid for $R^2$, and cyclopentanecarboxylic acid for $R^3$.

Preparation of Compound A12: (R)-4-isobutyl-3-(4-methylpentyl)-1-(4-((S)-2-(3-phenylpropyl)-4,5-dihydro-1H-imidazol-4-yl)butyl)imidazolidine-2-thione Compound A12 was synthesized with Boc-D-leucine reagent used for $R^1$, 4-methylvaleric acid for $R^2$, and 4-phenylbutyric acid for $R^3$.

Preparation of Compound A13: (4R)-1-(4-((4S)-2-(sec-butyl)-4,5-dihydro-1H-imidazol-4-yl)butyl)-3-(2-cyclohexylethyl)-4-isobutylimidazolidine-2-thione Compound A13 was synthesized with Boc-D-leucine reagent used for $R^1$, cyclohexylacetic acid for $R^2$, and (+/−)-2-methylbutyric acid for $R^3$.

Preparation of Compound A15: (R)-3-(2-cyclohexylethyl)-4-isobutyl-1-(4-((S)-2-(3-phenylpropyl)-4,5-dihydro-1H-imidazol-4-yl)butyl)imidazolidine-2-thione Compound A15 was synthesized with Boc-D-leucine reagent used for $R^1$, cyclohexylacetic acid for $R^2$, and 4-phenylbutyric acid for $R^3$.

Preparation of Compound A19: (4R)-1-(4-((4S)-2-(sec-butyl)-4,5-dihydro-1H-imidazol-4-yl)butyl)-3-(4-methylpentyl)-4-phenylimidazolidine-2-thione Compound A19 was synthesized with Boc-D-phenylglycine reagent used for $R^1$, 4-methylvaleric acid for $R^2$, and (+/−)-2-methylbutyric acid for $R^3$.

Preparation of Compound A20: (R)-1-(4-((S)-2-cyclopentyl-4,5-dihydro-1H-imidazol-4-yl)butyl)-3-(4-methylpentyl)-4-phenylimidazolidine-2-thione Compound A20 was synthesized with Boc-D-phenylglycine reagent used for $R^1$, 4-methylvaleric acid for $R^2$, and cyclopentanecarboxylic acid for $R^3$.

Preparation of Compound A21: (R)-3-(4-methylpentyl)-4-phenyl-1-(4-((S)-2-(3-phenylpropyl)-4,5-dihydro-1H-imidazol-4-yl)butyl)imidazolidine-2-thione Compound A21 was synthesized with Boc-D-phenylglycine reagent used for $R^1$, 4-methylvaleric acid for $R^2$, and 4-phenylbutyric acid for $R^3$.

Preparation of Compound A22: (4R)-1-(4-((4S)-2-(sec-butyl)-4,5-dihydro-1H-imidazol-4-yl)butyl)-3-(2-cyclohexylethyl)-4-phenylimidazolidine-2-thione Compound A22 was synthesized with Boc-D-phenylglycine reagent used for $R^1$, cyclohexylacetic acid for $R^2$, and (+/−)-2-methylbutyric acid for $R^3$.

Preparation of Compound A24: (R)-3-(2-cyclohexylethyl)-4-phenyl-1-(4-((S)-2-(3-phenylpropyl)-4,5-dihydro-1H-imidazol-4-yl)butyl)imidazolidine-2-thione Compound A24 was synthesized with Boc-D-phenylglycine reagent Cell Preparation and Culture Pre-coating culture plates: On the day before the experiment, 96-well plates were pre-coated by plating 50 μL of poly-D-lysine solution (PDL, 0.5 mg/mL) in each well. The next morning, the plates were washed four or five times with HBSS or PBS (150 μL/rinse), then left in buffer until cell plating Preparing the cells: A timed pregnant rat carrying E18 embryos was euthanized using an IACUC approved method. In a laminar flow hood, the embryos were removed and placed in a petri dish containing Hank's Balanced Salt Solution (HBSS) with 20 mM HEPES, pH 7.3. Pup brains were dissected (see Meberg et al., Methods cell Biol 71:111-127 (2003)) and hippocampi were collected in 15 mL a conical tube containing Hibernate E with SM1 (2% v/v).

Dissociation media was prepared by combining 4.5 mL of Hibernate E (without SM1) with 0.5 mL of trypsin and 100 μl of DNAse solution. The medium over the hippocampi was carefully removed and replaced with dissociation solution, then incubated at 37° C. for 15-20 minutes, occasionally swirling the tube.

Using flame polished cotton plugged Pasteur pipettes, the dissociation media was removed, and then 5 mL of Hibernate E containing SM1 were added. The tube was swirled to thoroughly wash the tissue. The tissue was allowed to settle to the bottom of the tube, and the rinse solution was carefully removed. This step was repeated 5 times to dilute out trypsin and DNAse and remove any debris from lysed cells.

The final rinse media was removed from the tube and 1 pipette-full (1-2 mL) of Hibernate E with SM1 was added. Using the flame-polished Pasteur pipette (pre-wetted with rinse media), the tube was triturated until all cells had dissociated and no visible chunks of tissue remained. Fewer than ten triturations were typically performed. The volume was adjusted to 8-12 mL using Hibernate E containing SM1, the well was mixed and cell concentration was determined.

Plating: The cells were diluted in culture media (NbActiv4 Cell-culture media) to a final concentration of 10,000 cells/mL. The HBSS was aspirated from PDL coated plates, and 150 µL of cell solution was loaded in the middle 48 wells at 1500 cells per well. Water was loaded in the outer wells to decrease evaporation from edge wells. Cells were allowed to adhere for 2 hours in tissue culture incubator prior to treatment.

Treatment: Compounds were diluted to various concentrations to provide 6 dose response concentrations of 500 ng/mL, 250 ng/mL, 125 ng/mL, 62.5 ng/mL, 31.25 ng/mL, and 15.625 ng/mL. The plates were cultured for 48 hours, exposed to the compound at the various dose response concentrations.

Fixing the cultures: The culture medium was removed from the plates and immediately replaced with 100-200 µL of warm (37° C.) 4% paraformaldehyde ("PFA") solution in phosphate-buffered saline ("PBS"). The cells were fixed for 15-20 minutes at room temperature, and then rinsed with PBS (200 µl/well×3).

Staining and imaging: The PBS was removed and replaced with 100 µL of blocking/permeabilization buffer (PBS, 0.2% fish gelatin, 0.03% Triton X-100, 0.02% $NaN_3$), then incubated overnight at 4° C. To this was added 100 µL of primary antibody solution (mouse anti-Beta III tubulin in blocking buffer) and incubate overnight at 4° C. The wells were rinsed with PBS (200 µl×3), which was then removed and replaced with 100 µL of secondary antibody solution (Goat anti-mouse Alexa 488, 10 µg/ml Hoechst 33342, 0.2% fish gelatin, 0.02% azide, in PBS). The plate was shaken gently on a rotating shaker for 2 hours, then rinsed with PBS (200 µl×5).

The plate was imaged using a Cellomics ArrayScan VTI in 2 different channels for nuclear staining (Hoechst) and cell body/neurite staining (βIII-tubulin). Typically, nine fields per well were imaged with a 5× objective and automatically traced by the Neuronal Profiling Bioapplication. To get reproducible results, at least 200-300 valid neurons were measured per condition.

The data for each compound as assessed in the above assay are presented in the below Table, showing the neurite growth length (% NTL) upon exposure to the compound at each concentration.

| # | 500 ng/mL | 250 ng/mL | 125 ng/mL | 62.5 ng/mL | 31.25 ng/mL | 15.625 ng/mL |
|---|---|---|---|---|---|---|
| A1 | 323 | 209 | 169 | 155 | 116 | 92 |
| A2 | 324 | 265 | 214 | 176 | 138 | 114 |
| A3 | 347 | 257 | 160 | 124 | 100 | 116 |
| A4 | 358 | 246 | 196 | 143 | 121 | 102 |
| A5 | 304 | 246 | 251 | 188 | 158 | 105 |
| A6 | 243 | 247 | 210 | 122 | 122 | 101 |
| A7 | 294 | 267 | 166 | 150 | 135 | 97 |
| A8 | 322 | 257 | 231 | 168 | 128 | 95 |
| A9 | 297 | 238 | 70 | 118 | 102 | 88 |
| A10 | 240 | 259 | 254 | 223 | 180 | 123 |
| A11 | 256 | 264 | 273 | 266 | 215 | 135 |
| A12 | 240 | 266 | 237 | 194 | 145 | 127 |
| A13 | 264 | 253 | 253 | 262 | 179 | 159 |
| A14 | 249 | 277 | 283 | 271 | 256 | 195 |
| A15 | 247 | 267 | 201 | 199 | 135 | 114 |
| A16 | 264 | 236 | 268 | 254 | 216 | 131 |
| A17 | 263 | 238 | 312 | 254 | 255 | 170 |
| A18 | 224 | 240 | 257 | 247 | 197 | 145 |
| A19 | 276 | 266 | 264 | 253 | 179 | 121 |
| A20 | 273 | 278 | 249 | 280 | 234 | 174 |
| A21 | 225 | 254 | 259 | 172 | 170 | 114 |
| A22 | 228 | 222 | 246 | 257 | 201 | 139 |
| A23 | 186 | 232 | 262 | 260 | 252 | 182 |
| A24 | 184 | 222 | 254 | 252 | 209 | 144 |
| A25 | 280 | 256 | 302 | 297 | 256 | 190 |
| A26 | 230 | 271 | 286 | 306 | 272 | 251 |
| A27 | 221 | 245 | 269 | 238 | 174 | 185 |

Compound potency values were estimated using linear interpolation. As shown in the Table, below, the compounds described herein can exhibit nanomolar potency at a 200% and 300% effective dose.

| # | $ED_{200\%}$ (nM) | $ED_{300\%}$ (nM) |
|---|---|---|
| A8 | 130 | 282 |
| A14 | 4 | >543 |
| A16 | 10 | 53 |
| A17 | 4 | 25 |
| A18 | 25 | 461 |
| A23 | 7 | 91 |
| A25 | 5 | 54 |
| A26 | 2 | >520 |
| A27 | 17 | >471 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising"

will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

What is claimed:

1. A compound of Formula (I), or a pharmaceutically acceptable salt thereof:

$$R^3-HET-(CH_2)_m-N\overset{R^1}{\underset{\underset{X}{\overset{\|}{N}}}{\bigg|}}\overset{}{\underset{R^2}{}} \quad (I)$$

wherein:
m is 3, 4, or 5;
n is 1 or 2;
HET is $C_{3-7}$heterocycloalkyl;
each X independently is S or O;
$R^1$ is unsubstituted $C_{1-6}$ alkyl, $C_{0-3}$ alkylene-$C_{3-7}$ cycloalkyl, $C_{0-3}$ alkylene-$C_{3-7}$heterocycloalkyl, phenyl, or $C_{0-3}$ alkylene-$C_{2-6}$ heteroaryl;
$R^2$ is unsubstituted $C_{1-6}$ alkyl, $C_{1-3}$ alkylene-$C_{3-7}$ cycloalkyl, $C_{1-3}$ alkylene-$C_{3-7}$heterocycloalkyl, or $C_{1-3}$ alkylene-$C_{2-6}$ heteroaryl; and
$R^3$ is $C_{1-8}$ alkyl, $C_{0-3}$ alkylene-$C_{3-7}$ cycloalkyl, $C_{0-3}$ alkylene-$C_{3-7}$heterocycloalkyl, $C_{0-3}$ alkylene-$C_{6-10}$ aryl, or $C_{0-3}$ alkylene-$C_{2-6}$ heteroaryl; and
each heterocycloalkyl and heteroaryl group independently has 1, 2, or 3 ring heteroatoms selected from N, O, and S.

2. The compound or salt of claim 1, wherein m is 4.
3. The compound or salt of claim 1, wherein n is 1.
4. The compound or salt of claim 3, wherein X is S.
5. The compound or salt of claim 1, wherein HET comprises dihydroimidazolyl, piperazinyl, diketopiperazinyl, $C_{2-5}$ cyclic guanidinyl, $C_{2-5}$ cyclic ureayl, $C_{2-5}$cyclic thioureayl, aziridinyl, oxiranyl, thiiranyl, azirinyl, oxirenyl, thiirenyl, azetidinyl, oxetanyl, thetanyl, azetenyl, oxetenyl, thetenyl, pyrrolidinyl, tetrahydrofuranyl, tetrahydrothiophenyl, piperidinyl, tetrahydropyranyl, tetrahydrothiopyranyl, pyranyl, thiopyranyl, or morpholinyl.

6. The compound or salt of claim 5, wherein HET is

[structure shown]

7. The compound or salt of claim 1, wherein $R^1$ is $C_{1-6}$alkyl or phenyl.
8. The compound or salt of claim 7, wherein $C_{1-6}$ alkyl is methyl, ethyl, propyl, isopropyl, butyl, 2-butyl, or isobutyl.
9. The compound of claim 1, wherein $R^1$ is:
(i) methyl or isobutyl; or
(ii) $CH_2$-cyclohexyl, or
(iii) phenyl, or
(iv) 3-methylpyridinyl.
10. The compound or salt of claim 1, wherein $R^2$ is:

[structures shown], and

11. The compound or salt of claim 1, wherein $R^3$ is $C_{1-8}$alkyl, $C_{0-3}$alkylene-$C_{3-7}$ cycloalkyl, $C_{1-3}$alkylene-$C_{6-10}$ aryl, or $C_{1-3}$alkylene-$C_{2-6}$ heteroaryl.
12. The compound or salt of claim 11, wherein $R^3$ is:
(i) s-butyl; or
(ii)

[structures shown]

-continued

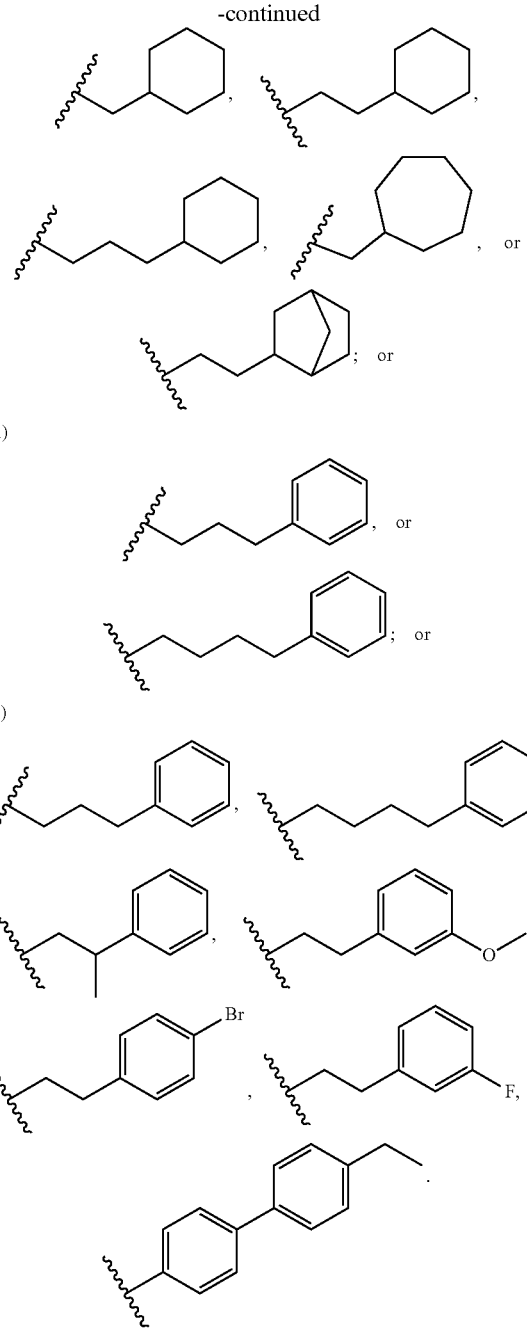

(iii)

(iv)

13. The compound or salt of claim 1, wherein:
m is 4;
n is 1;
X is S;
HET is

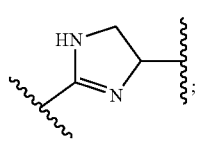 [SMILES: *C1=NC(*)CN1]

$R^1$ is $C_{1-6}$ alkyl or phenyl;
$R^2$ is $C_{1-3}$ alkylene-$C_{3-7}$ cycloalkyl, and
$R^3$ is $C_{1-8}$alkyl, $C_{0-3}$ alkylene-$C_{3-7}$cycloalkyl, or $C_{1-3}$ alkylene-$C_{6-10}$aryl.

14. The compound or salt of claim 1, wherein $R^2$ is ethyl.

15. A compound or pharmaceutically acceptable salt thereof having a structure as listed in Table A:

TABLE A

| Compound # | $R^1$ | $R^2$ | $R^3$ |
|---|---|---|---|
| A1 | methyl | 4-methylpentyl | s-butyl |
| A2 | methyl | 4-methylpentyl | cyclopentyl |
| A3 | methyl | 4-methylpentyl | (CH$_2$)$_3$—Ph |
| A4 | methyl | CH$_2$CH$_2$-cyclohexyl | s-butyl |
| A5 | methyl | CH$_2$CH$_2$-cyclohexyl | cyclopentyl |
| A6 | methyl | CH$_2$CH$_2$-cyclohexyl | (CH$_2$)$_3$—Ph |
| A7 | methyl | CH$_2$-4-methylcyclohexyl | s-butyl |
| A8 | methyl | CH$_2$-4-methylcyclohexyl | cyclopentyl |
| A9 | methyl | CH$_2$-4-methylcyclohexyl | (CH$_2$)$_3$—Ph |
| A10 | isobutyl | 4-methylpentyl | s-butyl |
| A11 | isobutyl | 4-methylpentyl | cyclopentyl |
| A12 | isobutyl | 4-methylpentyl | (CH$_2$)$_3$—Ph |
| A13 | isobutyl | CH$_2$CH$_2$-cyclohexyl | s-butyl |
| A14 | isobutyl | CH$_2$CH$_2$-cyclohexyl | cyclopentyl |
| A15 | isobutyl | CH$_2$CH$_2$-cyclohexyl | (CH$_2$)$_3$—Ph |
| A16 | isobutyl | CH$_2$-4-methylcyclohexyl | s-butyl |
| A17 | isobutyl | CH$_2$-4-methylcyclohexyl | cyclopentyl |
| A18 | isobutyl | CH$_2$-4-methylcyclohexyl | (CH$_2$)$_3$—Ph |
| A19 | phenyl | 4-methylpentyl | s-butyl |
| A20 | phenyl | 4-methylpentyl | cyclopentyl |
| A21 | phenyl | 4-methylpentyl | (CH$_2$)$_3$—Ph |
| A22 | phenyl | CH$_2$CH$_2$-cyclohexyl | s-butyl |
| A23 | phenyl | CH$_2$CH$_2$-cyclohexyl | cyclopentyl |
| A24 | phenyl | CH$_2$CH$_2$-cyclohexyl | (CH$_2$)$_3$—Ph |
| A25 | phenyl | CH$_2$-4-methylcyclohexyl | s-butyll |
| A26 | phenyl | CH$_2$-4-methylcyclohexyl | cyclopentyl |
| A27 | phenyl | CH$_2$-4-methylcyclohexyl | (CH$_2$)$_3$—Ph. |

16. The compound or salt of claim 15, selected from the group consisting of

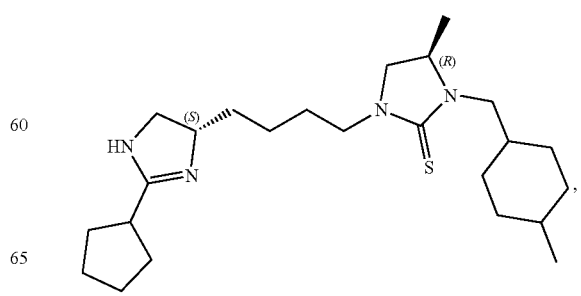

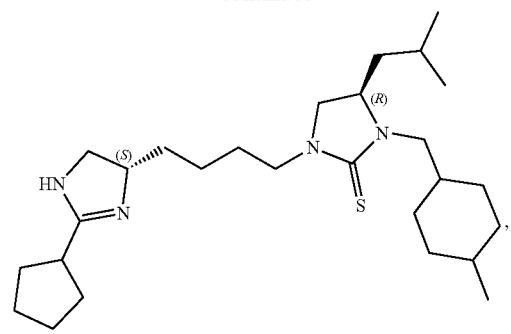
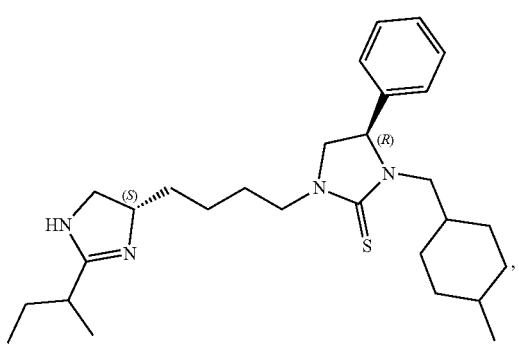
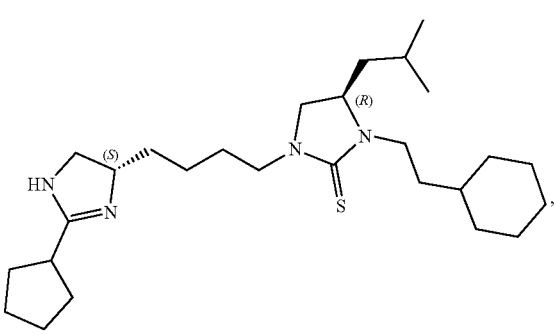
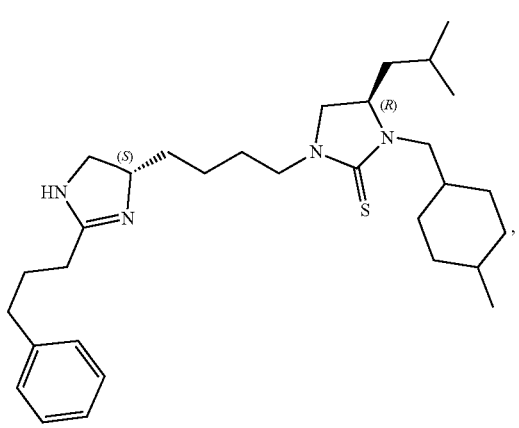
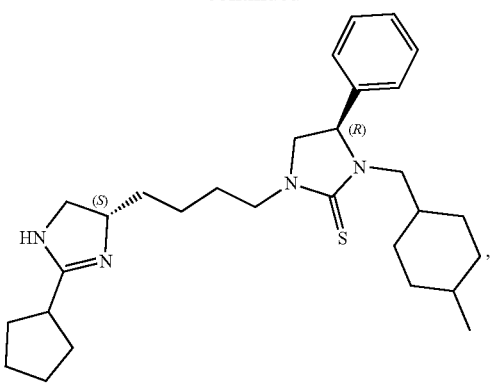
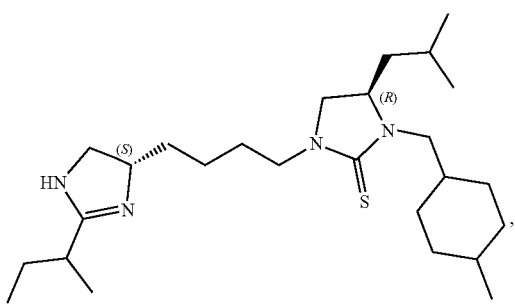
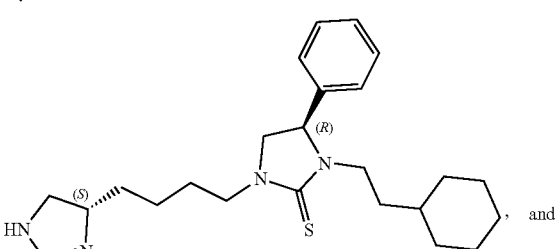
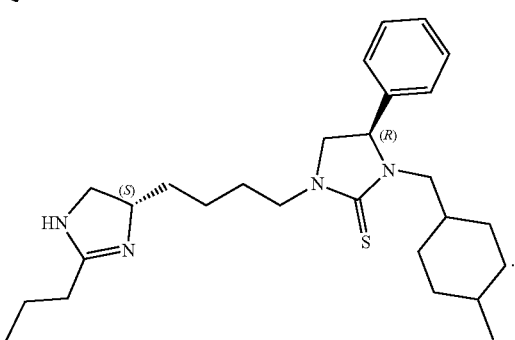, and
17. A pharmaceutical composition comprising the compound or salt of claim 1 and a pharmaceutically acceptable carrier.
18. A method of treating a central nervous system (CNS) disorder or a peripheral nervous system (PNS) disorder associated with neuronal and/or axonal damage in a subject in need thereof, comprising administering to the subject the compound or salt of claim 1, in an amount effective to repair neuronal and/or axonal damage and treat the CNS disorder or the PNS disorder.

19. A method of treating nerve degeneration in a subject undergoing cancer therapy, comprising administering to the subject the compound or salt of claim 1, in an amount effective to treat the nerve degeneration.

* * * * *

UNITED STATES PATENT AND TRADEMARK OFFICE
CERTIFICATE OF CORRECTION

PATENT NO. : 11,981,660 B2
APPLICATION NO. : 16/982946
DATED : May 14, 2024
INVENTOR(S) : Vance Lemmon et al.

Page 1 of 1

It is certified that error appears in the above-identified patent and that said Letters Patent is hereby corrected as shown below:

On the Title Page

Item (57), Lines 5-6, "and pharmaceutically acceptable salts and compositions including the same." should be at Line 9, after the structure.

Item (57), Line 7, "(I)" should be -- (I); --.

In the Claims

At Column 36, Line 17, "isobutyl; or" should be -- isobutyl, or --.

At Column 36, Line 51, "and" should be -- or --.

At Column 37, Line 67, "cycloalkyl, and" should be -- cycloalkyl; and --.

At Column 38, Line 47, "s-butyll" should be -- s-butyl --.

Signed and Sealed this
Nineteenth Day of November, 2024

Katherine Kelly Vidal
*Director of the United States Patent and Trademark Office*